(12) United States Patent
Beckman et al.

(10) Patent No.: US 7,819,800 B2
(45) Date of Patent: Oct. 26, 2010

(54) FULLY AUTOMATED IRIS SEAL FOR HAND ASSISTED LAPAROSCOPIC SURGICAL PROCEDURES

(75) Inventors: Andrew T. Beckman, Cincinnati, OH (US); Paul T. Franer, Cincinnati, OH (US); Michael D. Cronin, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 312 days.

(21) Appl. No.: 11/611,193

(22) Filed: Dec. 15, 2006

(65) Prior Publication Data
US 2008/0146884 A1   Jun. 19, 2008

(51) Int. Cl.
*A61B 1/32* (2006.01)
(52) U.S. Cl. .................. 600/208; 600/201; 600/204
(58) Field of Classification Search ................. 600/206, 600/208, 204
See application file for complete search history.

(56) References Cited

U.S. PATENT DOCUMENTS

| | | | |
|---|---|---|---|
| 563,645 | A | 7/1896 | Bitting |
| 564,645 | A | 7/1896 | Queen |
| 2,739,587 | A | 3/1956 | Scholl |
| 3,111,943 | A | 11/1963 | Orndorff |
| 3,332,417 | A | 7/1967 | Blanford et al. |
| 3,347,226 | A | 10/1967 | Harrower |
| 3,347,227 | A | 10/1967 | Harrower |
| 3,397,692 | A | 8/1968 | Creager, Jr. et al. |
| 5,100,420 | A | 3/1992 | Green et al. |
| 5,104,383 | A | 4/1992 | Shichman |
| 5,171,249 | A | 12/1992 | Stefanchik et al. |
| 5,197,955 | A | 3/1993 | Stephens et al. |
| 5,292,330 | A | 3/1994 | Shutt |
| 5,324,268 | A | 6/1994 | Yoon |
| 5,337,754 | A | 8/1994 | Heaven et al. |
| 5,366,478 | A | 11/1994 | Brinkerhoff et al. |
| 5,385,552 | A | 1/1995 | Haber et al. |
| 5,437,683 | A | 8/1995 | Neumann et al. |

(Continued)

FOREIGN PATENT DOCUMENTS

EP    0776180    6/1997

(Continued)

OTHER PUBLICATIONS

Search Report for PCT/US2007/087385 dated May 29, 2008.

(Continued)

*Primary Examiner*—Thomas C Barrett
*Assistant Examiner*—Michael T Schaper
(74) *Attorney, Agent, or Firm*—Frost Brown Todd LLC

(57) ABSTRACT

A laparoscopic device assembly provides a tubular diaphragm twist seal that responds to a slight rotation of an actuating ring in a first direction by coupling a motor spring power assisted rotation of a bottom circumference of the twist seal achieves a pneumatic seal in an adjustable access channel defined by the state of the twist seal for maintaining an insufflated body cavity for a hand assisted laparoscopic surgical procedure. A slight rotation of the actuating ring in an opposite second direction releases compression spring energy and energy in the twisted state of the twist seal so that an upper circumference of the twist seal is allowed to open the adjustable access channel.

19 Claims, 32 Drawing Sheets

U.S. PATENT DOCUMENTS

| | | |
|---|---|---|
| 5,449,141 A * | 9/1995 | Gillett et al. ............... 251/4 |
| 5,460,170 A | 10/1995 | Hammerslag |
| 5,480,410 A | 1/1996 | Cuschieri et al. |
| 5,514,133 A | 5/1996 | Golub et al. |
| 5,522,791 A | 6/1996 | Leyva |
| 5,524,644 A | 6/1996 | Crook |
| 5,526,536 A | 6/1996 | Cartmill |
| 5,545,179 A | 8/1996 | Williamson, IV |
| 5,640,977 A | 6/1997 | Leahy et al. |
| 5,649,550 A | 7/1997 | Crook |
| 5,653,705 A | 8/1997 | de la Torre et al. |
| 5,653,717 A | 8/1997 | Ko et al. |
| 5,672,168 A | 9/1997 | de la Torre et al. |
| 5,741,298 A | 4/1998 | MacLeod |
| 5,803,921 A | 9/1998 | Bonadio |
| 5,810,721 A | 9/1998 | Mueller et al. |
| 5,813,409 A | 9/1998 | Leahy et al. |
| 5,817,062 A | 10/1998 | Flom et al. |
| 5,853,395 A | 12/1998 | Crook et al. |
| 5,899,208 A | 5/1999 | Bonadio |
| 5,906,577 A | 5/1999 | Beane et al. |
| 5,925,064 A | 7/1999 | Meyers et al. |
| 5,947,922 A | 9/1999 | MacLeod |
| 5,957,913 A | 9/1999 | de la Torre et al. |
| 6,024,736 A | 2/2000 | de la Torre et al. |
| 6,033,426 A | 3/2000 | Kaji |
| 6,033,428 A | 3/2000 | Sardella |
| 6,048,309 A | 4/2000 | Flom et al. |
| 6,077,288 A | 6/2000 | Shimomura et al. |
| 6,110,154 A | 8/2000 | Shimomura et al. |
| 6,142,935 A | 11/2000 | Flom et al. |
| 6,142,936 A | 11/2000 | Beane et al. |
| 6,142,946 A | 11/2000 | Hwang et al. |
| 6,149,642 A | 11/2000 | Gerhart et al. |
| 6,159,200 A | 12/2000 | Verdura et al. |
| 6,165,184 A | 12/2000 | Verdura et al. |
| 6,228,022 B1 | 5/2001 | Friesem et al. |
| 6,254,534 B1 | 7/2001 | Butler et al. |
| 6,315,770 B1 | 11/2001 | de la Torre et al. |
| 6,319,246 B1 | 11/2001 | de la Torre et al. |
| 6,382,211 B1 | 5/2002 | Crook |
| 6,440,063 B1 | 8/2002 | Beane et al. |
| 6,450,983 B1 | 9/2002 | Rambo |
| 6,485,467 B1 | 11/2002 | Crook et al. |
| 6,536,277 B1 * | 3/2003 | Chuang ............... 73/319 |
| 6,540,983 B1 | 4/2003 | Adjei et al. |
| 6,578,577 B2 | 6/2003 | Bonadio et al. |
| 6,582,364 B2 | 6/2003 | Butler et al. |
| 6,589,167 B1 | 7/2003 | Shimomura et al. |
| 6,613,952 B2 | 9/2003 | Rambo |
| 6,623,426 B2 | 9/2003 | Bonadio et al. |
| 6,676,706 B1 | 1/2004 | Mears et al. |
| 6,723,044 B2 | 4/2004 | Pulford et al. |
| 6,808,520 B1 | 10/2004 | Fourkas et al. |
| 6,814,078 B2 | 11/2004 | Crook |
| 6,814,700 B1 | 11/2004 | Mueller et al. |
| 6,846,287 B2 | 1/2005 | Bonadio et al. |
| 2001/0037053 A1 | 11/2001 | Bonadio et al. |
| 2001/0047188 A1 | 11/2001 | Bonadio et al. |
| 2002/0002324 A1 | 1/2002 | McManus |
| 2002/0010389 A1 | 1/2002 | Butler et al. |
| 2002/0038077 A1 | 3/2002 | de la Torre et al. |
| 2002/0068923 A1 | 6/2002 | Caldwell et al. |
| 2002/0072762 A1 | 6/2002 | Bonadio et al. |
| 2002/0152559 A1 | 10/2002 | Muirhead |
| 2002/0183594 A1 | 12/2002 | Beane et al. |
| 2003/0062051 A1 | 4/2003 | Rambo |
| 2003/0078478 A1 | 4/2003 | Bonadio et al. |
| 2003/0187376 A1 | 10/2003 | Rambo |
| 2003/0192553 A1 | 10/2003 | Rambo |
| 2004/0015185 A1 | 1/2004 | Ewers et al. |
| 2004/0049099 A1 | 3/2004 | Ewers et al. |
| 2004/0049100 A1 | 3/2004 | Butler et al. |
| 2004/0073090 A1 | 4/2004 | Butler et al. |
| 2004/0092795 A1 | 5/2004 | Bonadio et al. |
| 2004/0092796 A1 | 5/2004 | Butler et al. |
| 2004/0093001 A1 | 5/2004 | Hamada |
| 2004/0097793 A1 | 5/2004 | Butler et al. |
| 2004/0127772 A1 | 7/2004 | Ewers et al. |
| 2004/0154624 A1 | 8/2004 | Bonadio et al. |
| 2004/0249248 A1 | 12/2004 | Bonadio et al. |
| 2004/0254426 A1 | 12/2004 | Wenchell |
| 2004/0260153 A1 | 12/2004 | Pulford et al. |
| 2004/0267096 A1 | 12/2004 | Caldwell et al. |
| 2005/0020884 A1 * | 1/2005 | Hart et al. ............... 600/206 |
| 2005/0137460 A1 | 6/2005 | Bertolero et al. |
| 2005/0148823 A1 | 7/2005 | Vaugh et al. |
| 2005/0222582 A1 * | 10/2005 | Wenchell ............... 606/108 |
| 2005/0241647 A1 | 11/2005 | Nguyen et al. |
| 2005/0283050 A1 | 12/2005 | Gundlapalli et al. |
| 2006/0084842 A1 | 4/2006 | Hart et al. |
| 2006/0135977 A1 | 6/2006 | Thompson et al. |
| 2006/0247500 A1 * | 11/2006 | Voegele et al. ............... 600/208 |
| 2008/0009834 A1 * | 1/2008 | Mialhe ............... 604/533 |
| 2008/0092034 A1 | 4/2008 | Lim et al. |
| 2008/0132765 A1 * | 6/2008 | Beckman et al. ............... 600/204 |

FOREIGN PATENT DOCUMENTS

| | | |
|---|---|---|
| EP | 0845960 | 6/1998 |
| EP | 0887047 | 12/1998 |
| EP | 0887048 | 12/1998 |
| EP | 0888755 | 1/1999 |
| EP | 1000583 | 5/2000 |
| EP | 1135070 | 9/2001 |
| EP | 1312318 | 5/2003 |
| EP | 1415610 | 5/2004 |
| EP | 1442710 | 8/2004 |
| WO | WO 93/11811 | 6/1993 |
| WO | WO 95/22289 | 8/1995 |
| WO | WO 95/24864 | 9/1995 |
| WO | WO 95/27468 | 10/1995 |
| WO | WO 96/10963 | 4/1996 |
| WO | WO 97/07742 | 3/1997 |
| WO | WO 98/48724 | 11/1998 |
| WO | WO 99/03416 | 1/1999 |
| WO | WO 99/25268 | 5/1999 |
| WO | WO 00/24326 | 5/2000 |
| WO | WO 00/32116 | 6/2000 |
| WO | WO 00/32117 | 6/2000 |
| WO | WO 00/32120 | 6/2000 |
| WO | WO 00/54676 | 9/2000 |
| WO | WO 00/54677 | 9/2000 |
| WO | WO 01/08581 | 2/2001 |
| WO | WO 01/26558 | 4/2001 |
| WO | WO 01/45568 | 6/2001 |
| WO | WO 02/34108 | 5/2002 |
| WO | WO 03/028523 | 4/2003 |
| WO | WO 03/061480 | 7/2003 |
| WO | WO 03/077726 | 9/2003 |
| WO | WO 2004/026153 | 4/2004 |
| WO | WO 2004/030547 | 4/2004 |
| WO | WO 2004/054456 | 7/2004 |
| WO | WO 2004/075730 | 9/2004 |
| WO | WO 2004/075741 | 9/2004 |
| WO | WO 2004/096012 | 11/2004 |
| WO | WO 2004/103161 | 12/2004 |
| WO | WO 2005/009257 | 2/2005 |
| WO | WO 2005009257 A2 * | 2/2005 |
| WO | WO 2006/061356 | 6/2006 |

| WO | WO 2006061356 A1 * 6/2006 |

OTHER PUBLICATIONS

U.S. Appl. No. 11/548,325, filed Oct. 11, 2006, Lim et al.
Abstract for EP 0845960.
Abstract for EP 0776180.
Abstract for EP 1135070.
International Search Report dated May 28, 2008 for Application No. PCT/US2007/087372.

\* cited by examiner

FULLY AUTOMATED IRIS SEAL FOR HAND ASSISTED LAPAROSCOPIC SURGICAL PROCEDURES

CROSS REFERENCE TO RELATED APPLICATIONS

The present application is related to two commonly-owned U.S. patent applications filed on even date herewith, the disclosures of which are hereby incorporated by reference in their entirety: (1) Ser. No. 11/611,215, entitled "Handoscopy Interwoven Layered Seal Laparoscopic Disk" to Cropper et al. and (2) Ser. No. 11/611,167, entitled "Resiliently Supported Seal Cap for Hand Assisted Laparoscopic Surgical Procedures" to Kistler et al.

FIELD OF THE INVENTION

The invention generally relates to surgical access systems that facilitate sealed access across a body wall and into a body cavity during a laparoscopic surgical procedure.

BACKGROUND OF THE INVENTION

Abdominal surgery typically involves an incision in the abdominal wall large enough to accommodate a surgeon's hands, multiple instruments, and illumination of the body cavity. While large incisions simplify access to the body cavity during a surgery, it also increases trauma, requires extended recovery time, and can result in unsightly scars. In response to these drawbacks, minimally invasive surgical methods have been developed.

In minimally invasive abdominal surgery, or laparoscopic surgery, several smaller incisions are made into the abdominal wall. One of the openings is used to inflate the abdominal cavity with gas, which lifts the abdominal wall away from underlying organs and provides space to perform the desired surgery. This process is referred to as insufflation of the body cavity. Additional openings may be used to accommodate cannulas or trocars for illuminating and viewing the cavity, as well as instruments involved in actually performing the surgery, e.g., instruments to manipulate, cut, or resect organs and tissue.

Hand Assisted Laparoscopic Surgical (HALS) procedures are gaining increased acceptance as combining advantages of open surgery (e.g., tactile feedback) yet have some of the advantages of reduced scarring, reduced recovery time, and reduced incidence of complications of closed procedures. Laparoscopic disks are often used to provide an adjustable opening that allows insertion of the surgeon's hand to the insufflated body cavity, yet provide significant pneumatic sealing with or without the presence of the surgeon's hand.

While generally-known laparoscopic disks successfully support HALS procedures, improvements to increase patient and surgeon comfort and to enhance performance are desired.

DESCRIPTION OF THE FIGURES

The accompanying drawings, which are incorporated in and constitute a part of this specification, illustrate embodiments of the invention, and, together with the general description of the invention given above, and the detailed description of the embodiments given below, serve to explain the principles of the present invention.

DETAILED DESCRIPTION OF THE INVENTION

Figure 1:
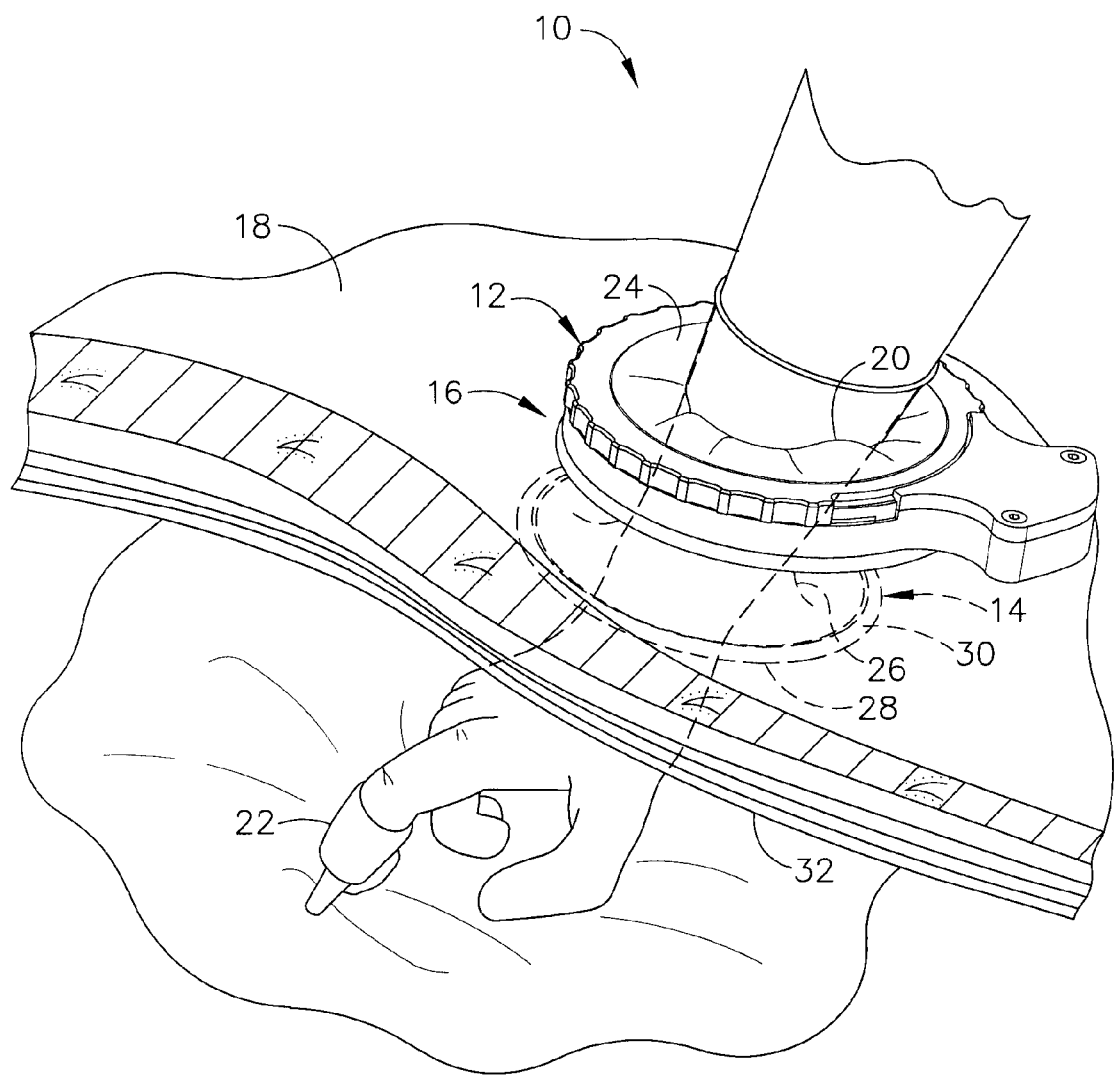
FIG. 1 is an environmental perspective view of a patient prepared for a Hand Assisted Laparoscopic Surgery (HALS) procedure by the insertion of a laparoscopic disk having a power assisted adjustable access channel.

Referring now to FIG. 1, the environment for performing an endoscopic surgical procedure within an abdomen is illustrated, herein referred to as Hand Assisted Laparoscopic Surgery (HALS). A surgeon places a hand through a HALS laparoscopic disk assembly 10 that includes an exteriorly visible laparoscopic disk (seal cap) 12 attached to a retractor skirt 14 that retracts (widens) an incision 16 through an abdominal wall 18 of a patient. The retractor skirt 14 may be permanently affixed or detachable. The laparoscopic disk 12 provides an adjustable access channel 20 that may be readily opened with assistance of stored energy so that an instrument, depicted as a fingertip surgical instrument 22, may be inserted through a tubular diaphragm twist seal 24 formed of materials such as isoprene, silicone, polyurethane and that provides an exterior pneumatic seal of the laparoscopic disk 12. The instrument 22 passes through the incision 16 that is retracted (i.e., made wider) by a resilient waist 26 of the retractor skirt 14 through a lower opening 28 of the retractor skirt 14 which is defined by a flexible ring 30 that forms a lip of the retractor skirt 14. The flexible ring 30 rests against an inner surface 32 of the abdominal wall 18 and surrounds the incision 16. The flexible ring 30 allows insertion in a deformed state through the incision 16 with subsequent rebounding to the depicted relaxed, circular shape.

Figure 2:
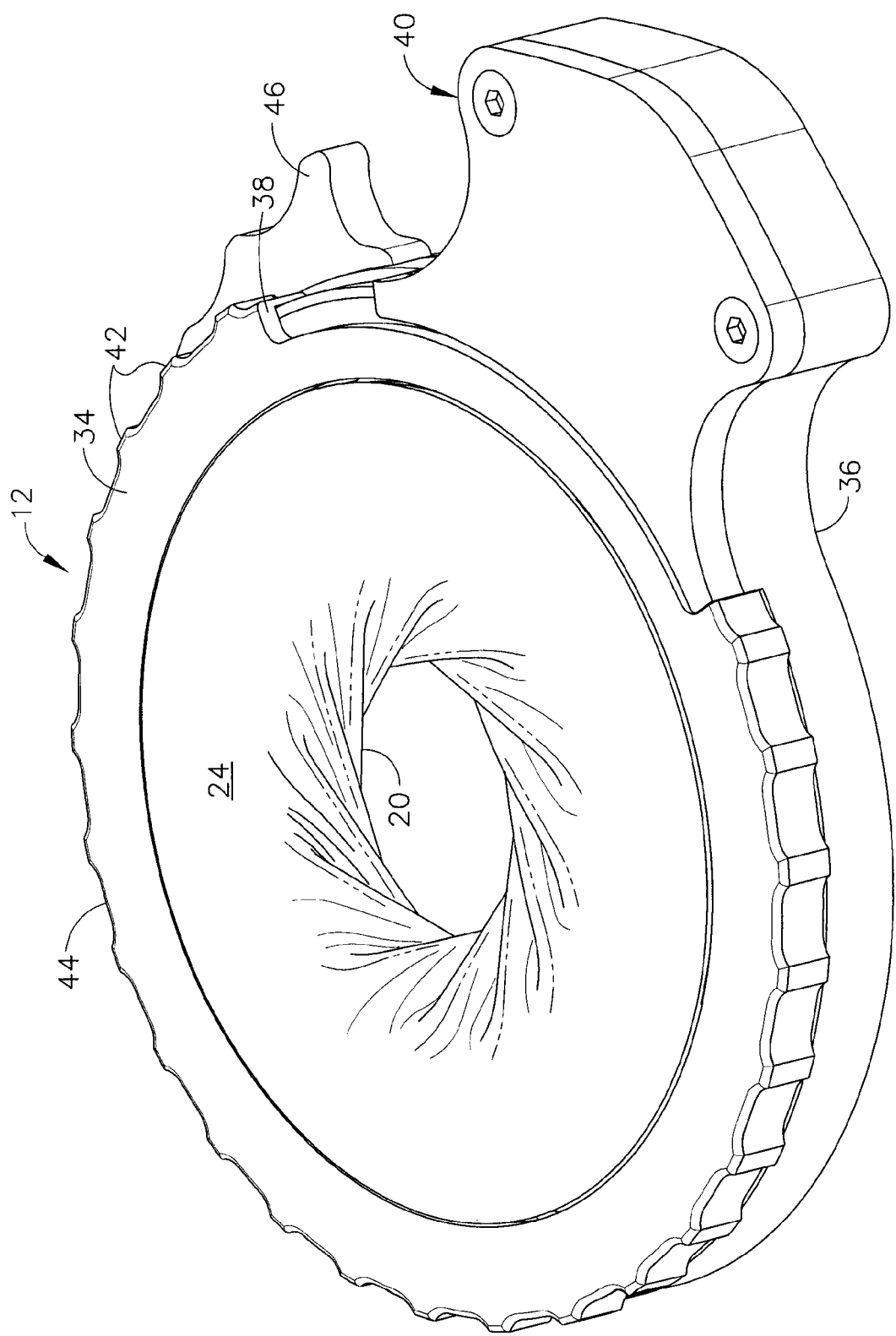
FIG. 2 is a perspective view of the laparoscopic disk of FIG. 1 having the power assisted adjustable access channel in an open condition in response to an upper actuating ring rotated to a counterclockwise most position.

In FIG. 2, the laparoscopic disk 12 may be readily positioned to an open state wherein the tubular diaphragm twist seal 24 is only slightly twisted by positioning an upper actuating ring 34 to a counterclockwise position as viewed from above relative to a lower base 36. A small outer portion 38 of the upper actuating ring 34 is cut away to allow this rotation to each side of a handle portion 40 of the lower base 36. Finger ridges 42 about a larger outer portion 44 of the upper actuating ring 34 enhance single hand operation when the palm grasps the handle portion 40. A winding actuator 46 extends outwardly proximate to and counterclockwise from the handle portion 40. Shipping and storage of the laparoscopic disk is typically in an open state to avoid reducing the service life of the twist seal 24.

Figure 3:
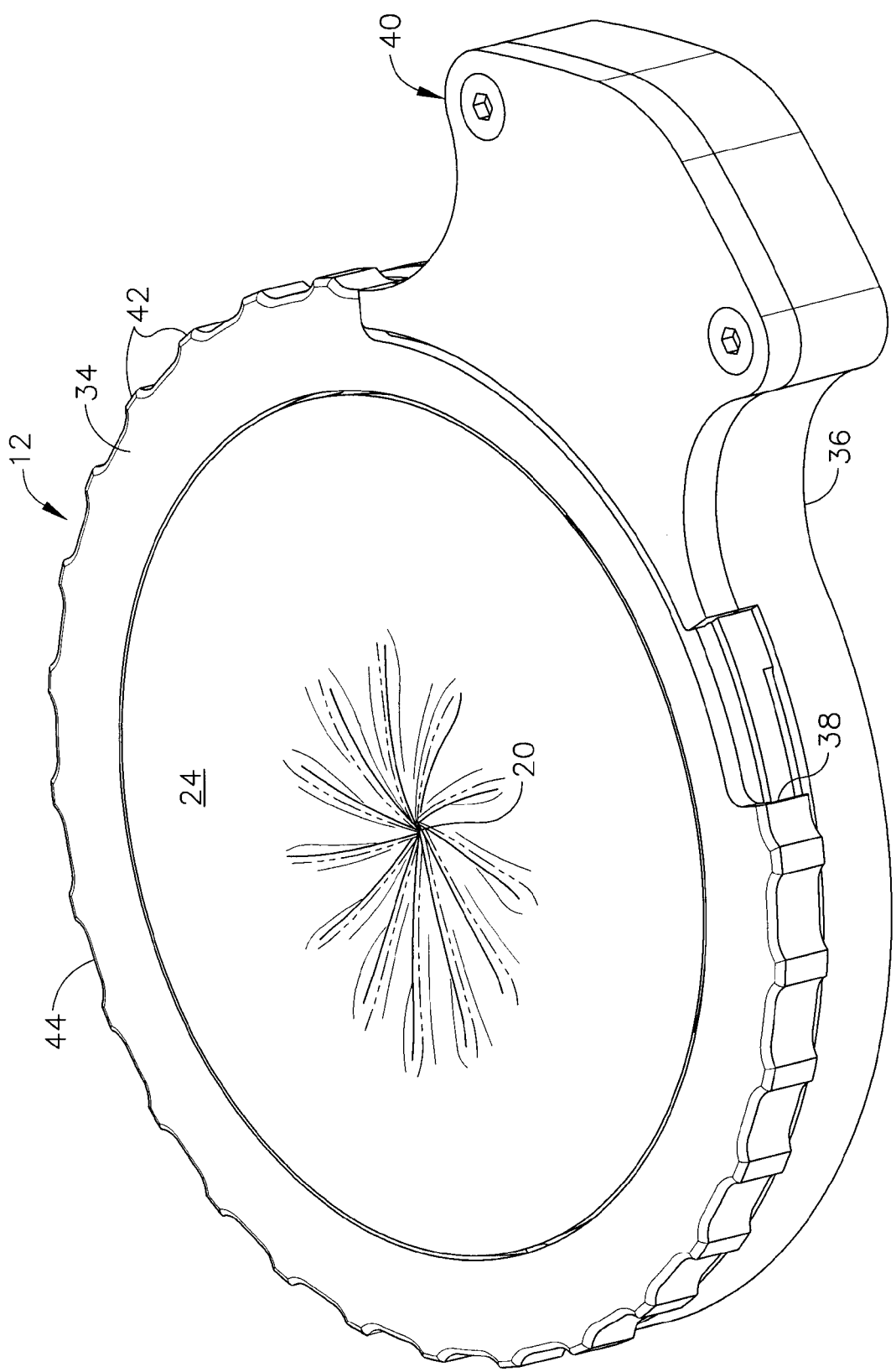
FIG. 3 is a perspective view of the laparoscopic disk of FIG. 1 having the power assisted adjustable access channel in a closed condition in response to the lower actuating ring rotated to a clockwise most position.

In FIG. 3, the laparoscopic disk 12 may be readily positioned to a closed state wherein the tubular diaphragm twist seal 24 is fully twisted by positioning the upper actuating ring 34 to a clockwise position as viewed from above. Thus, the small outer portion 38 of the actuating ring 34 is shifted by pushing on the finger ridges. The detachable winding actuator 46 is removed, which may be the typical arrangement during use since sufficient energy is stored within the laparoscopic disk 12 for repeated opening and closing. It should be appreciated that the laparoscopic disk 12 may be partially opened to an intermediate state by rotating the actuating ring 34 on a portion, which may be desirable given the diameter of the hand or tool to reduce the loss of pneumatic insufflation pressure. A fully open position may be desirable when performing extracorporalization, the removal of internal organs.

Figure 4:
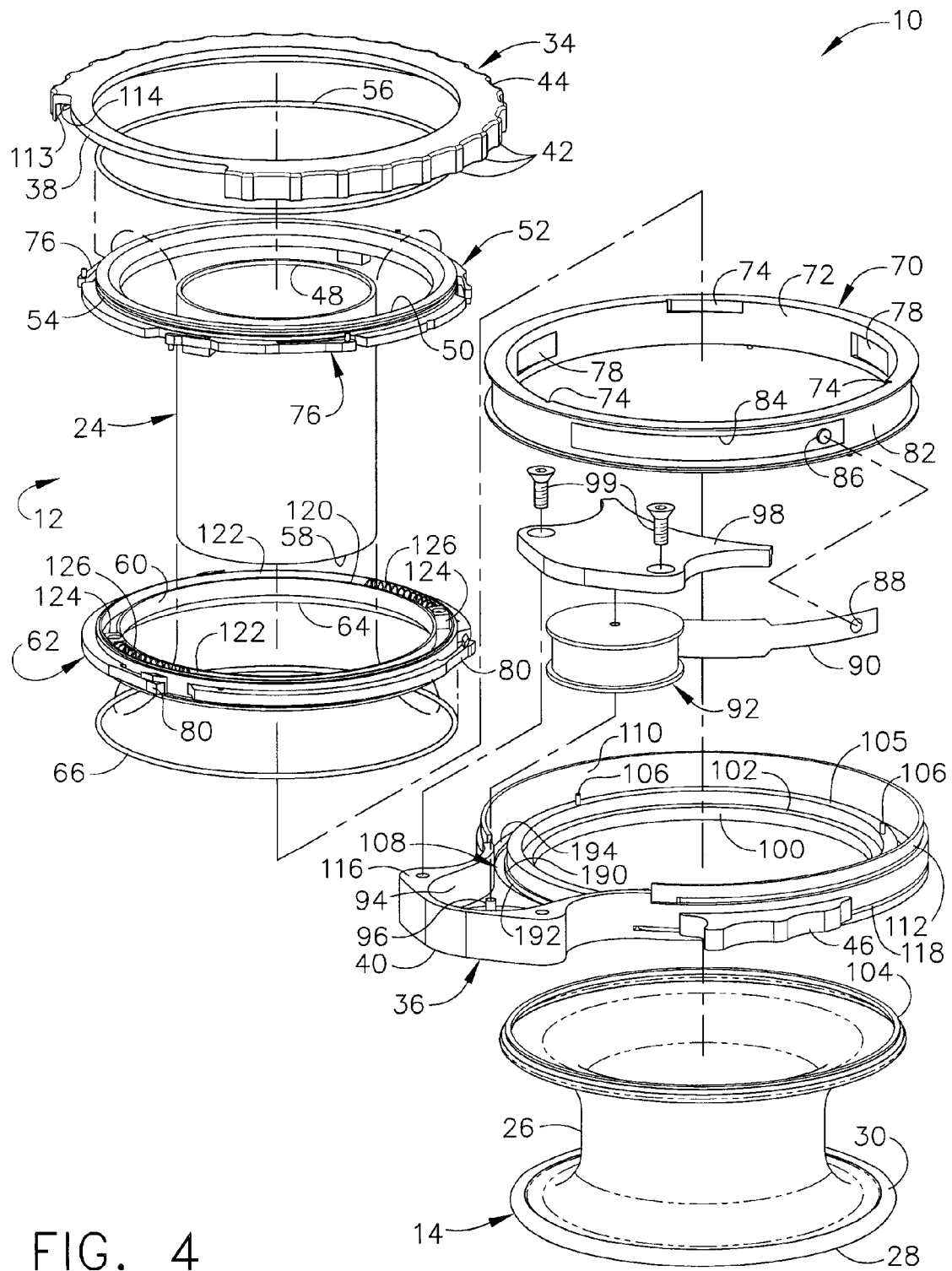
FIG. 4 is a perspective exploded view of the laparoscopic device assembly of FIG. 1.

In FIG. 4, the tubular diaphragm twist seal 24 is depicted prior to assembly in its cylindrical, relaxed shape. A top circumference 48 of the twist seal 24 passes up through an inner diameter 50 of an opening ring 52, which is positioned under the upper actuating ring 34, and stretched and curled outwardly and over an upwardly defined upper circular lip 54 of the opening ring 52, held thereon by a top O-ring 56. A bottom circumference 58 of the twist seal 24 extends downwardly through an inner diameter 60 of a lower stationary ring 62, which is positioned below the opening ring 52, and is stretched and curled outwardly and over a downwardly defined lower circular lip 64 on the stationary ring 62, held thereon by a lower O-ring 66.

A closure ring 70 has an inner diameter 72 with three radially spaced, clockwise ramped upper locking recesses 74 aligned for engagement with three radially spaced lock arms 76 extending outwardly from the encompassed opening ring 52. The inner diameter 72 of the closure ring 70 also has three radially spaced, counterclockwise-ramped lower stop recesses 78 aligned for engagement with three radially spaced stop arms 80 extending outwardly from the encompassed stationary ring 62.

Figure 22:
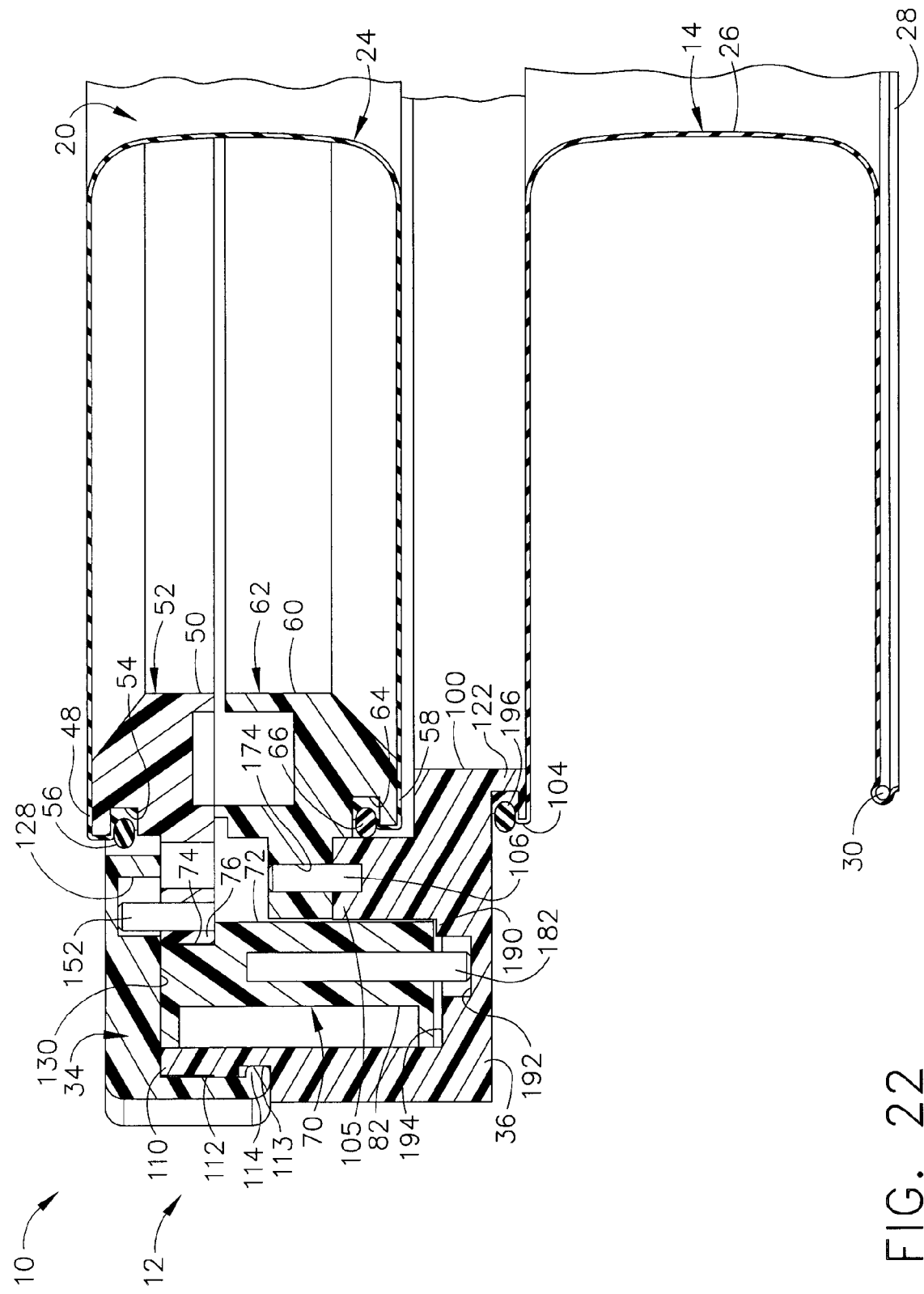
FIG. 22 is a left side view in elevation of the assembled laparoscopic device assembly of FIG. 21 with a staged cutaway through an upper pin of the opening ring, a counting hole of the stationary ring, and a winding pin of the closure ring.

An outer spool surface 82 of the closure ring 72 includes an elongate rectangular recess 84 having a button-headed post 86 attached near a counterclockwise end that is passed through a hole 88 in a narrow terminal tab 90 of a motor spring 92. The lower base 36 has a handle recess 94 that is shaped to receive the motor spring 92 upon an integral vertical spindle 96, with the recess 94 closed by a handle top cover 98 with fasteners 99. A central hole 100 in the lower base 36 below which extends a circular engagement lip 102 (FIG. 22), which receives an upper lip 104 of the retractor skirt 14, is within an upwardly projecting circular ridge 105 that includes several radially spaced upwardly projecting pins 106 that engage the undersurface of the stationary ring 62. A cylindrical recess 108 defined around the circular ridge 105 communicates with the handle recess 94 and is generally defined by an outer upward wall 110 whose outwardly reduced diameter portion 112 engages an outer groove 113 of a downward circular lip 114 from the larger outer portion 44 of the actuating ring 34 (FIG. 22). Each end of the outer upward wall 110 transitions to each side of a three sided handle wall 116 that defines the handle recess 94. A slit 118 passes laterally from adjacent to the handle portion 40 in a counterclockwise direction to receive the winding actuator 46.

It should be appreciated that the illustrative version incorporates a motor spring 92 but that other biasing springs may be incorporated consistent with aspects of the invention, such as a constant force spring and a clock spring. In addition, biasing springs may include extension or compression springs.

An upwardly open circular spring channel 120 is defined into the stationary ring 62 circumscribing the inner diameter 60, divided into two equal arcs 122 by a pair of channel blocks 124. A pair of compression springs 126 reside respectively in each arc 122 positioned to contact a respective channel block 124 from a counterclockwise side when viewed from above.

Figure 5:
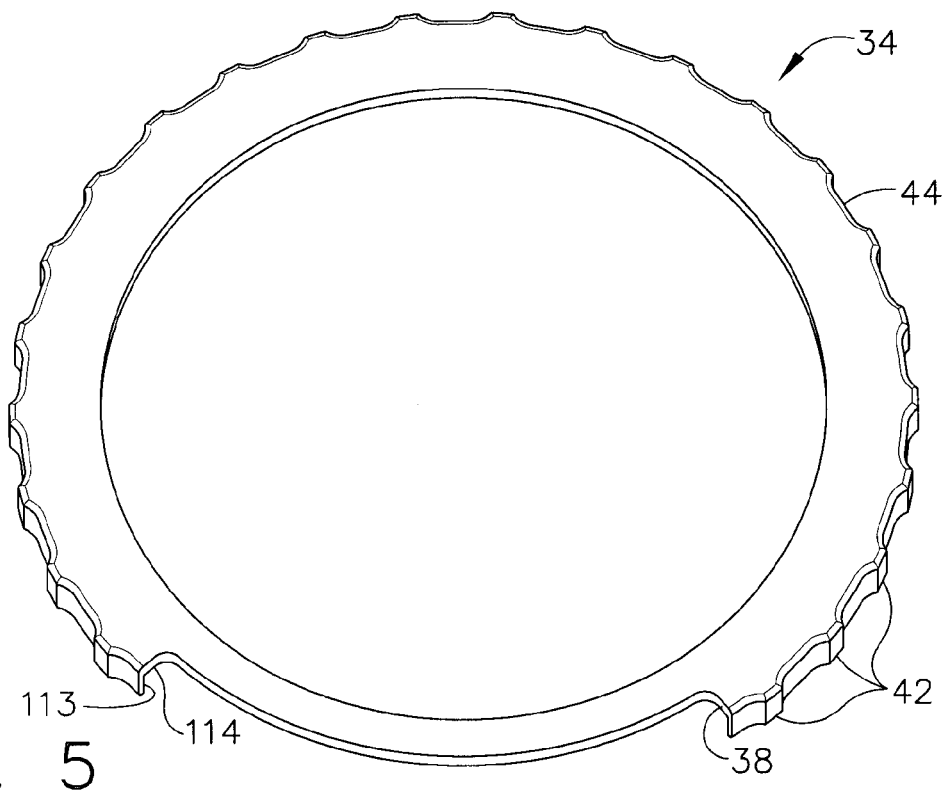
FIG. 5 is a top perspective view of the upper actuating ring of the laparoscopic device assembly of FIG. 1.
Figure 6:
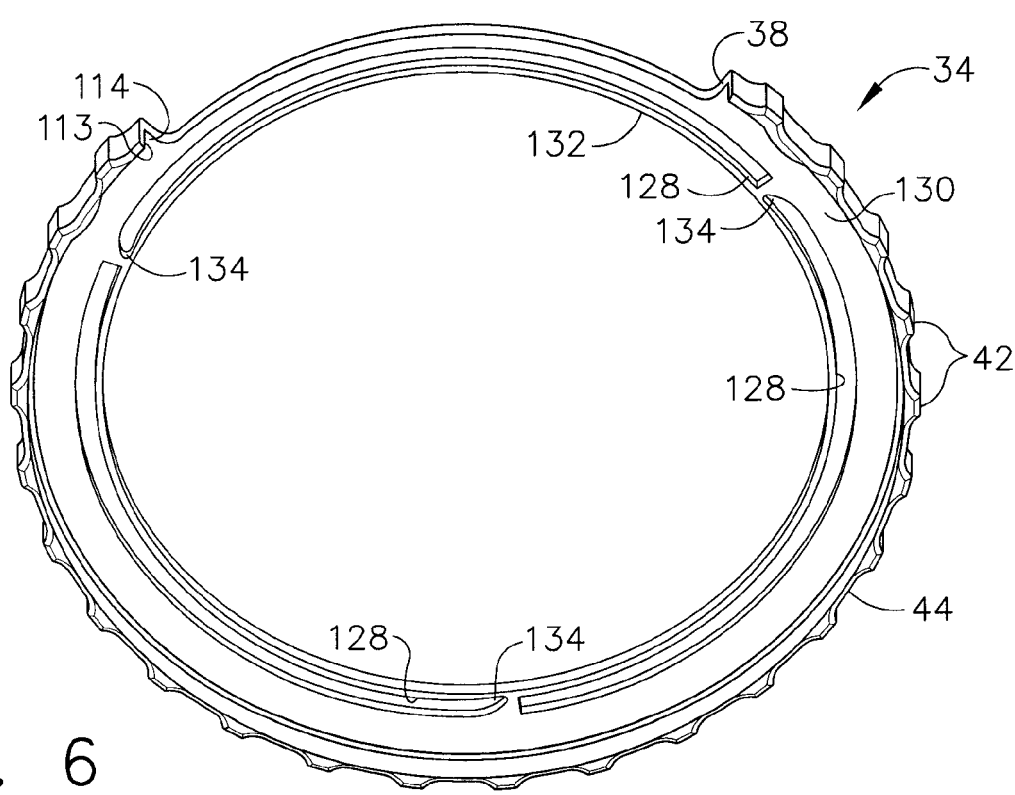
FIG. 6 is a bottom perspective view of the upper actuating ring of the laparoscopic device assembly of FIG. 1.

In FIGS. 5-6, the upper actuating ring 34 is depicted as having three arcing grooves 128 that form a nearly complete circular pattern into an undersurface 130 (FIG. 6) circumscribing a central large hole 132. Each clockwise termination 134 (counterclockwise as viewed from below as in FIG. 6) of each arcing groove 128 narrows by receding inwardly to a point and each counterclockwise termination 135 of the respective arcing groove 128 end in a squared off fashion.

Figure 7:
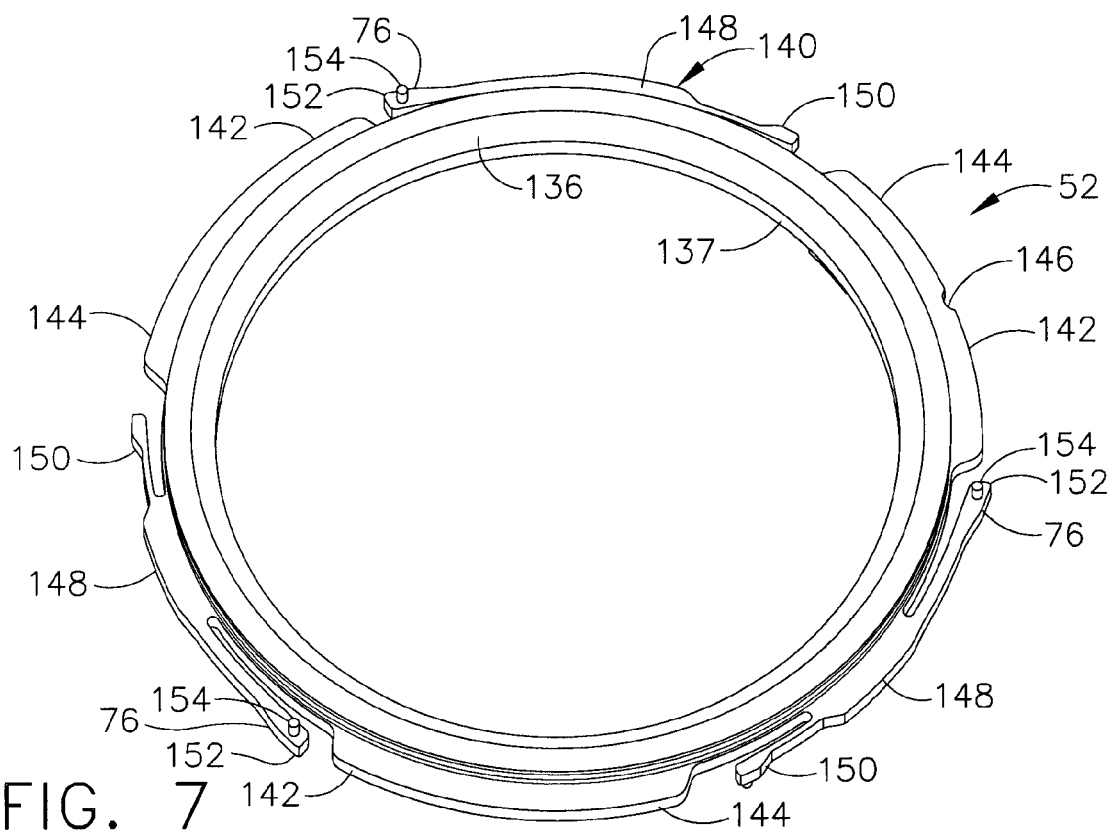
FIG. 7 is a top perspective view of an opening ring of the laparoscopic device assembly of FIG. 1.
Figure 8:
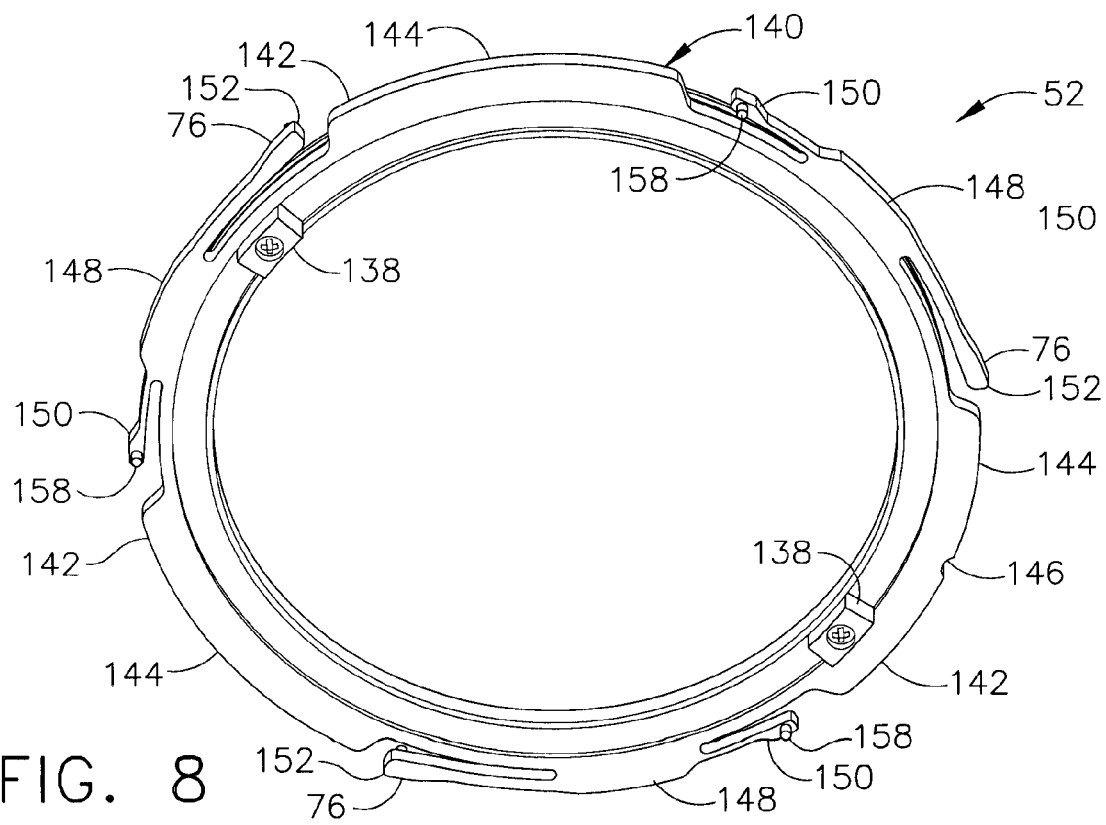
FIG. 8 is a bottom perspective view of the opening ring of the laparoscopic device assembly of FIG. 1.

In FIGS. 7-8, the opening ring 52 has an inner disk portion 136 defining an inner diameter 137 and with a pair of downwardly projecting spring blocks 138 (FIG. 8) on opposite sides registered to be received in respective ones of the two equal arcs 122 of the spring channel 120 of the stationary ring 62. An outer flange 140 attached to the inner disk portion 136 has three identical portions 142 that comprise a third of the circumference. Each includes a guiding portion 144 of about one-sixth of the circumference that is intended to contact for rotation the inner diameter 72 of the closure ring 70. One of the three guiding portions 144 includes an upper seal alignment notch 146 used during assembly. Each identical portion 142 also includes an arm mount 148 that branches into the counterclockwise projecting lock arm 76 and a clockwise (viewed from above) projecting release arm 150, with each generally extending to correspond to the encompassing inner diameter 72 of the closure ring 70. Each lock arm 76 resiliently extends slightly outwardly when not urged inwardly by contact with the closure ring 70 for extending a locking tip 152 into locking engagement to the upper locking recess 74 of the closure ring 70 (FIG. 4). An upward pin 154 (FIG. 7) extending from each locking tip 152 is registered to travel in a respective one of the three arcing grooves 128 formed in the undersurface 130 (FIG. 6). Each release arm 150 has a downward pin 158 (FIG. 8) registered to interact with the stationary ring 62.

Figure 9:
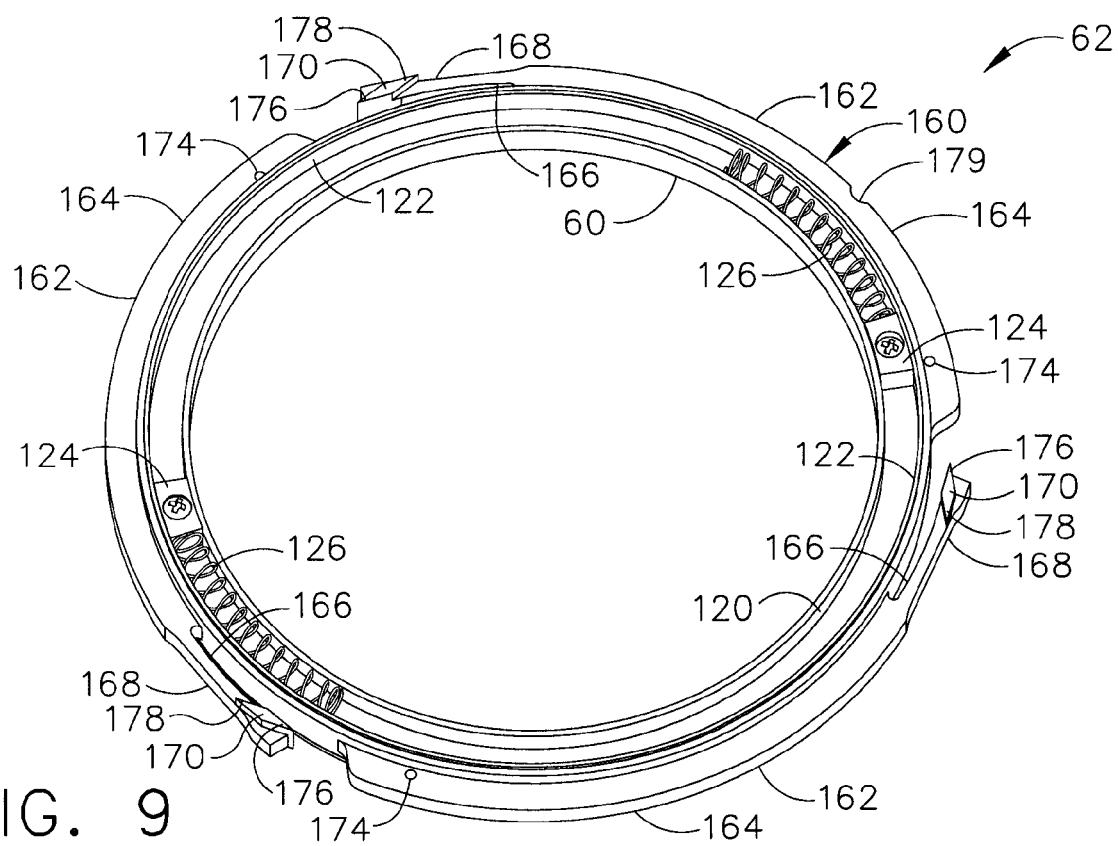
FIG. 9 is a top perspective view of a stationary ring of the laparoscopic device assembly of FIG. 1.
Figure 10:
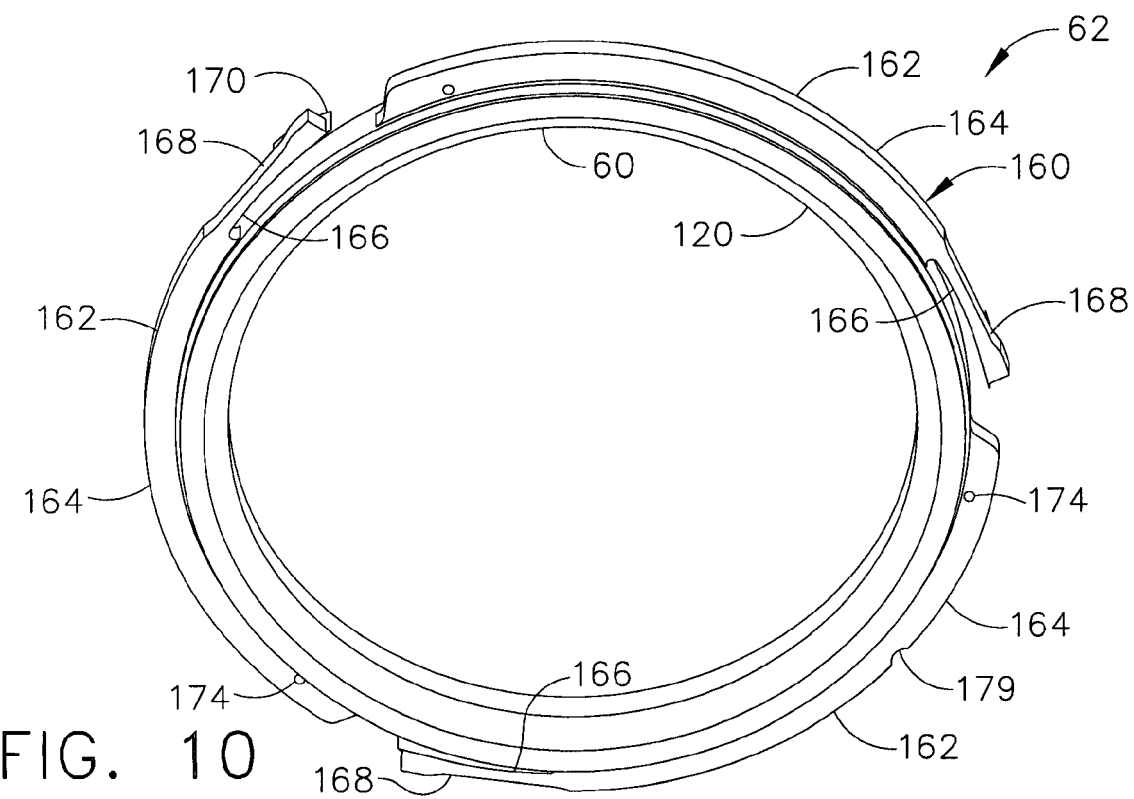
FIG. 10 is a bottom perspective view of the stationary ring of the laparoscopic device assembly of FIG. 1.

In FIGS. 9-10, each equal arc 122 of the spring channel 120 of the stationary ring 62 receives one of the spring blocks 138 (FIG. 8) from the opening ring 52. The stationary ring 62 has an outer flange 160 divided into three identical portions 162, with each including a holdout portion 164 of a substantial portion of a third of the circumference that is relieved on a counterclockwise portion 166 (when viewed from above) to form a counterclockwise projecting motor stop arm 168 with an upwardly projecting, parallelogram bypass key 170 outwardly biased to extend a motor stop corner 172 to engage the closure ring 70. Each holdout portion 164 includes a mounting hole 174 that receives one of the projecting pins 106 from the lower base 36. Each bypass key 170 presents a distal ramped surface 176 whose counterclockwise most corner is inward and a clockwise corner is outward with respect to the inner diameter 60, which thus requires that an opposite ramped surface 178 be parallel. Thus, the motor stop arm 168 tends to be deflected inwardly by a clockwise moving downward pin 158 of the opening ring 52 and is allowed to remain outwardly engaged to the closure ring 70 by a counterclockwise moving downward pin 158 of the opening ring 52. One of the holdout portions 164 includes a lower seal alignment notch 179 for reference during assembly.

Figure 11:
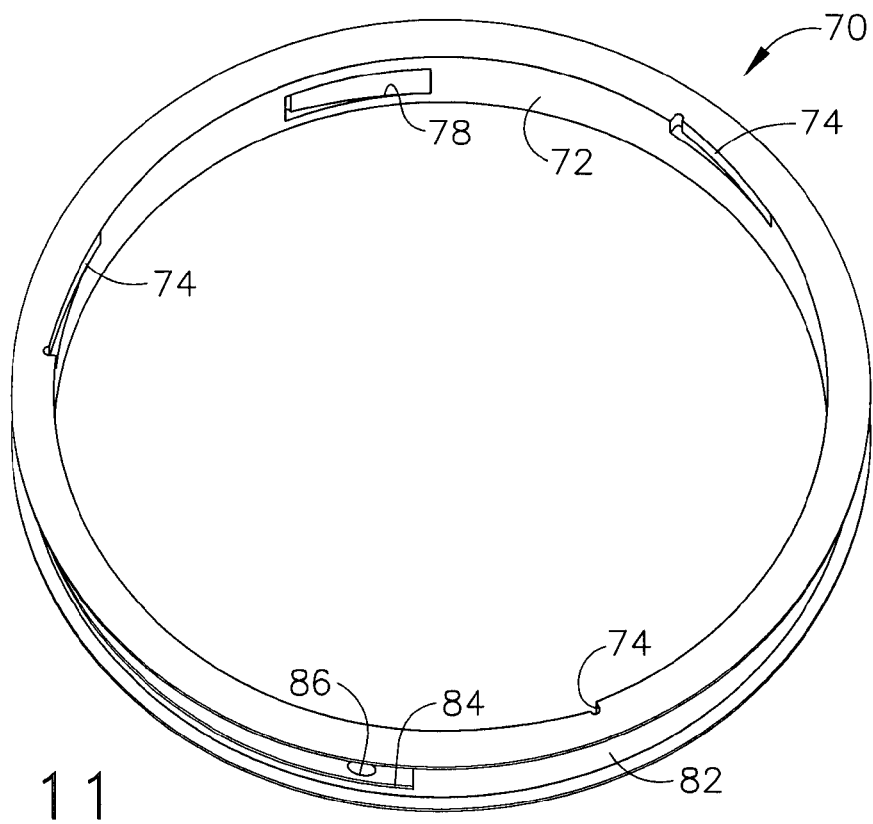
FIG. 11 is a top perspective view of a closure ring of the laparoscopic device assembly of FIG. 1.
Figure 12:
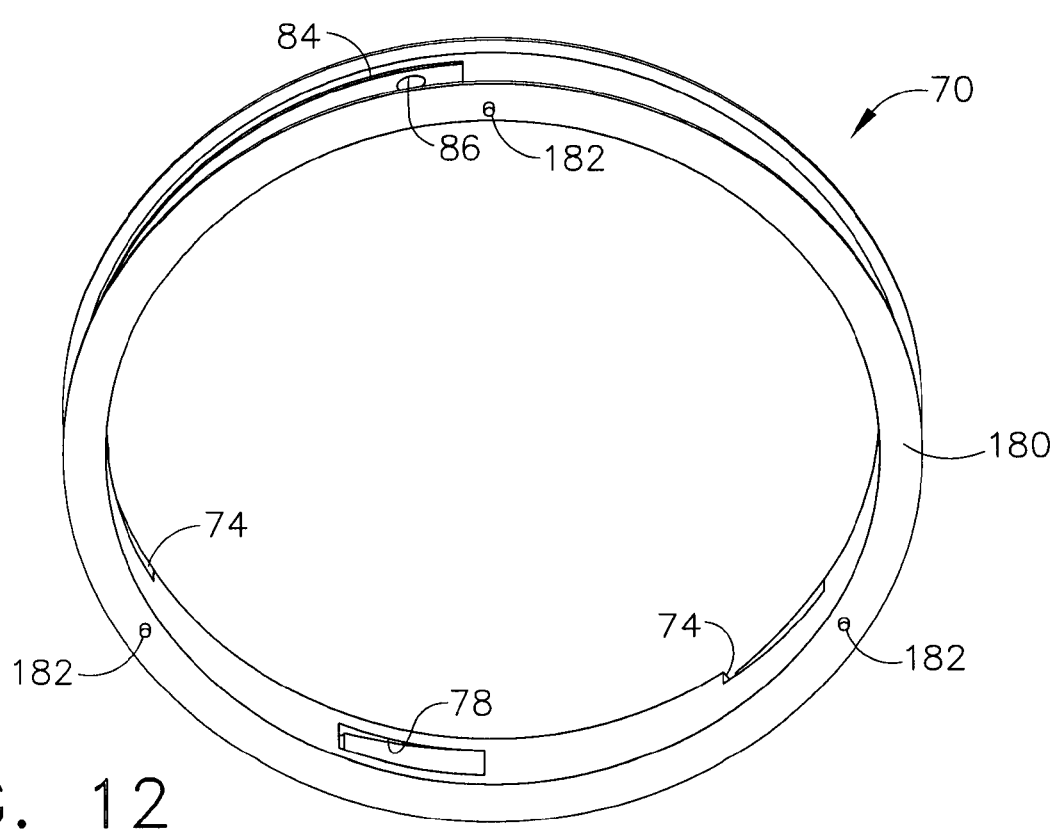
FIG. 12 is a bottom perspective view of the closure ring of the laparoscopic device assembly of FIG. 1.

In FIG. 11-12, the closure ring 70 is depicted in greater detail, including the upper locking recesses 74 aligned for engagement with the three radially spaced lock arms 76 extending outwardly from the encompassed opening ring 52 (FIGS. 7-8) and the three radially spaced, counterclockwise-ramped lower stop recesses 78 for engagement with the three radially spaced stop arms 80 extending outwardly from the encompassed stationary ring 62. In addition, in FIG. 12, A bottom surface 180 of the closure ring 70 has three radially spaced, downwardly projecting winding pins 182.

Figure 13:
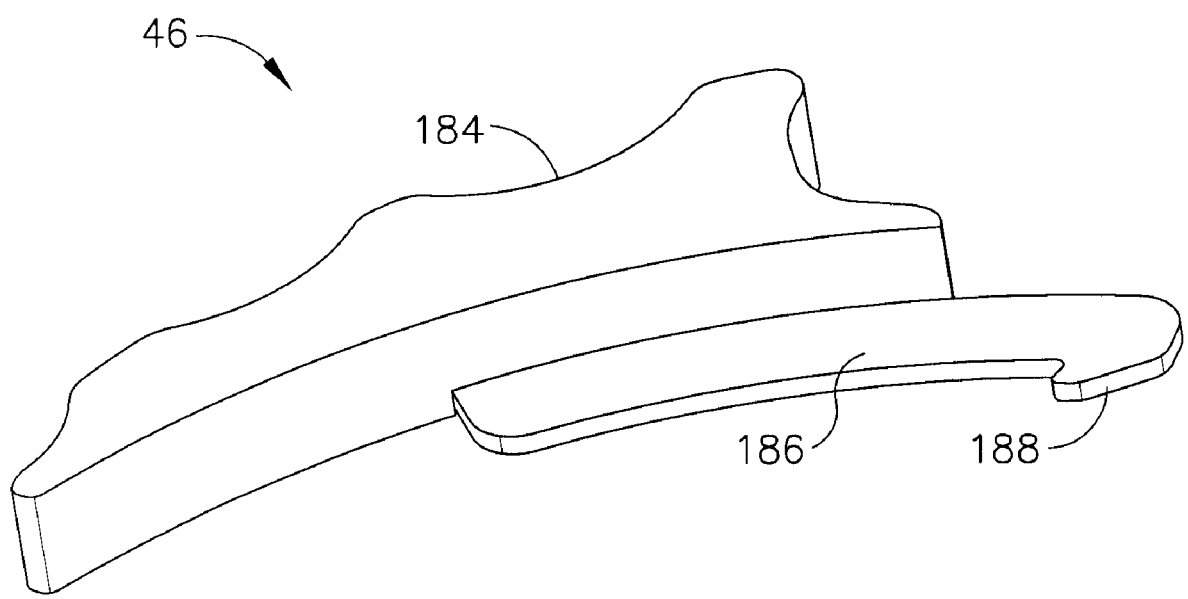
FIG. 13 is a perspective view of a winding actuator of the laparoscopic device of FIG. 2.

In FIG. 13, the winding actuator 46 has a molded external gripping portion 184 attached to a thin clockwise projecting winding arm 186 with a hooked end 188 shaped to engage the winding pins 182 (FIG. 12) for imposing a counterclockwise rotation to the closure ring 70 in opposition to the bias from the motor spring 92 (FIG. 4).

Figure 14:
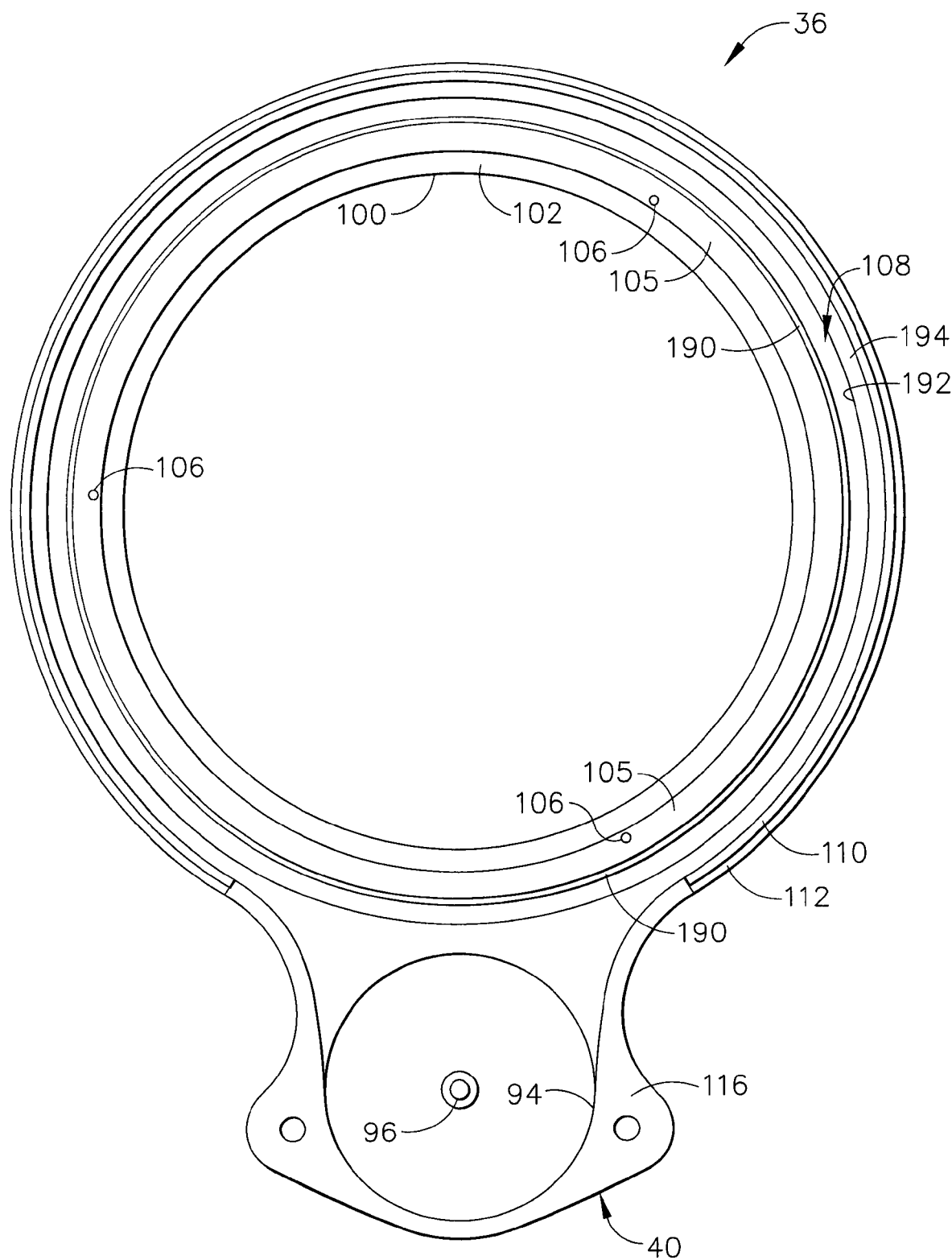
FIG. 14 is a top plan view of a lower base of the laparoscopic device assembly of FIG. 1.

In FIGS. 14 and 4, the lower base 36 is depicted as including a closure ring supporting surface 190 that closely circumscribes the upwardly projecting circular ridge 105 for supporting the bottom surface 180 of the closure ring 70. The closure ring 70 in turn is closely circumscribed by a winding pin groove 192 that receives the winding pins 182, which in turn is closely circumscribed by a hook supporting surface 194 of slightly deeper depth than the closure ring supporting surface 190 for guiding the winding arm 186 beneath the height of the bottom surface 180, and thus below the closure ring 70, as depicted in FIG. 15.

Figure 15:
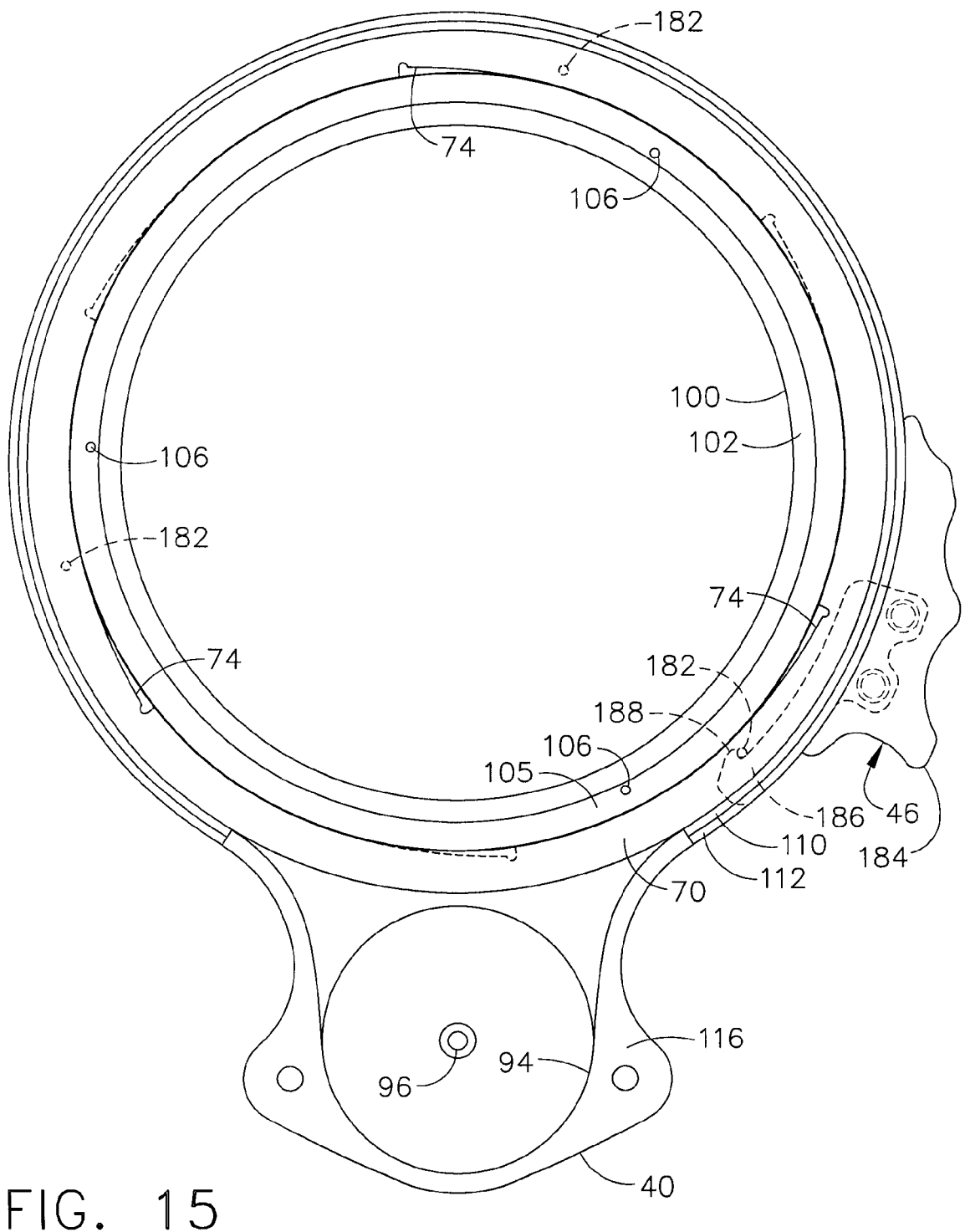
FIG. 15 is a top plan view of the closure ring and winding actuator installed onto the lower base of FIG. 14 during assembly of the laparoscopic device assembly of FIG. 1.
Figure 16:
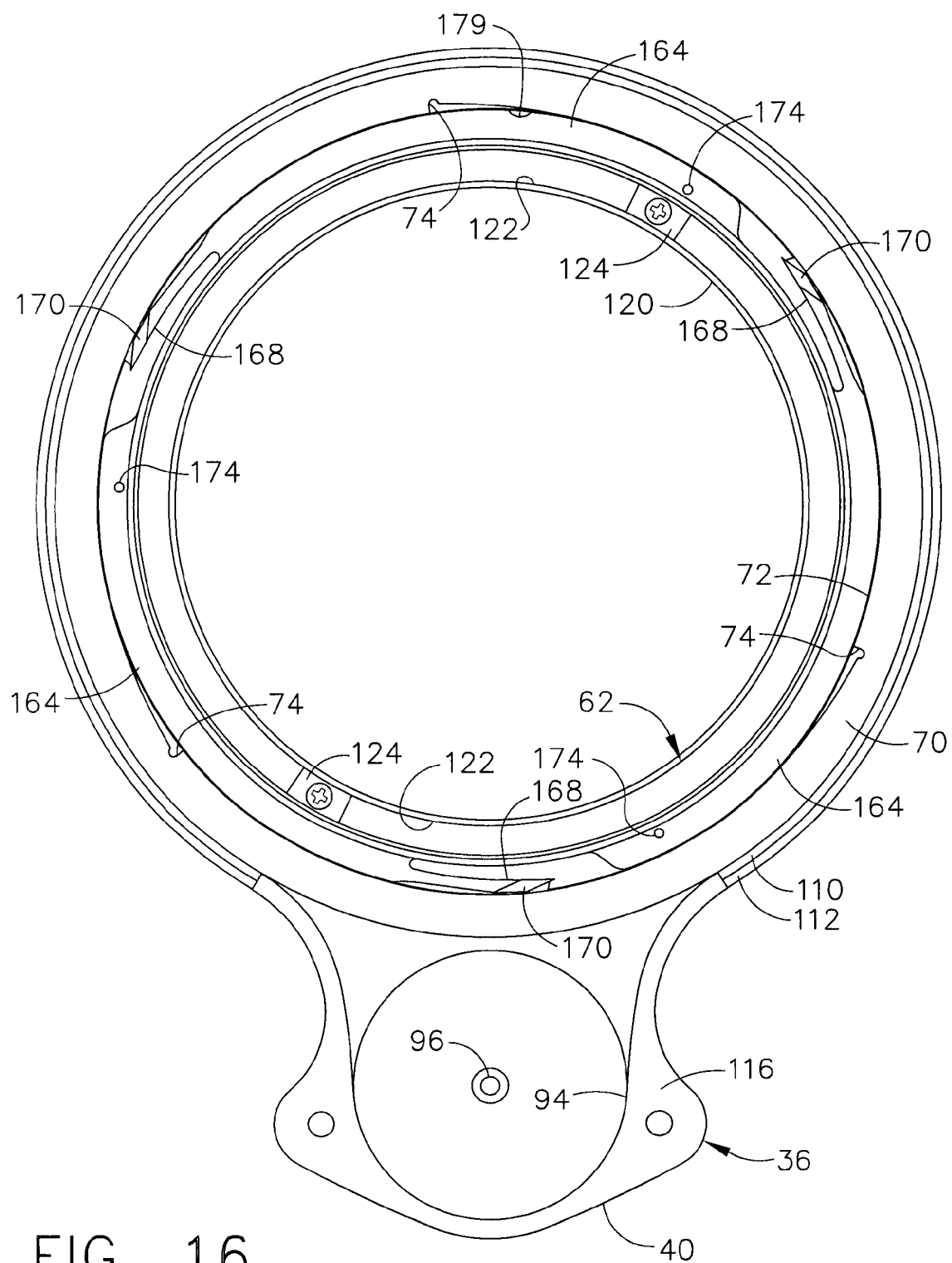
FIG. 16 is a top plan view of the stationary ring installed inside of the closure ring and lower base of FIG. 15 during assembly of the laparoscopic device assembly of FIG. 1.
Figure 17:
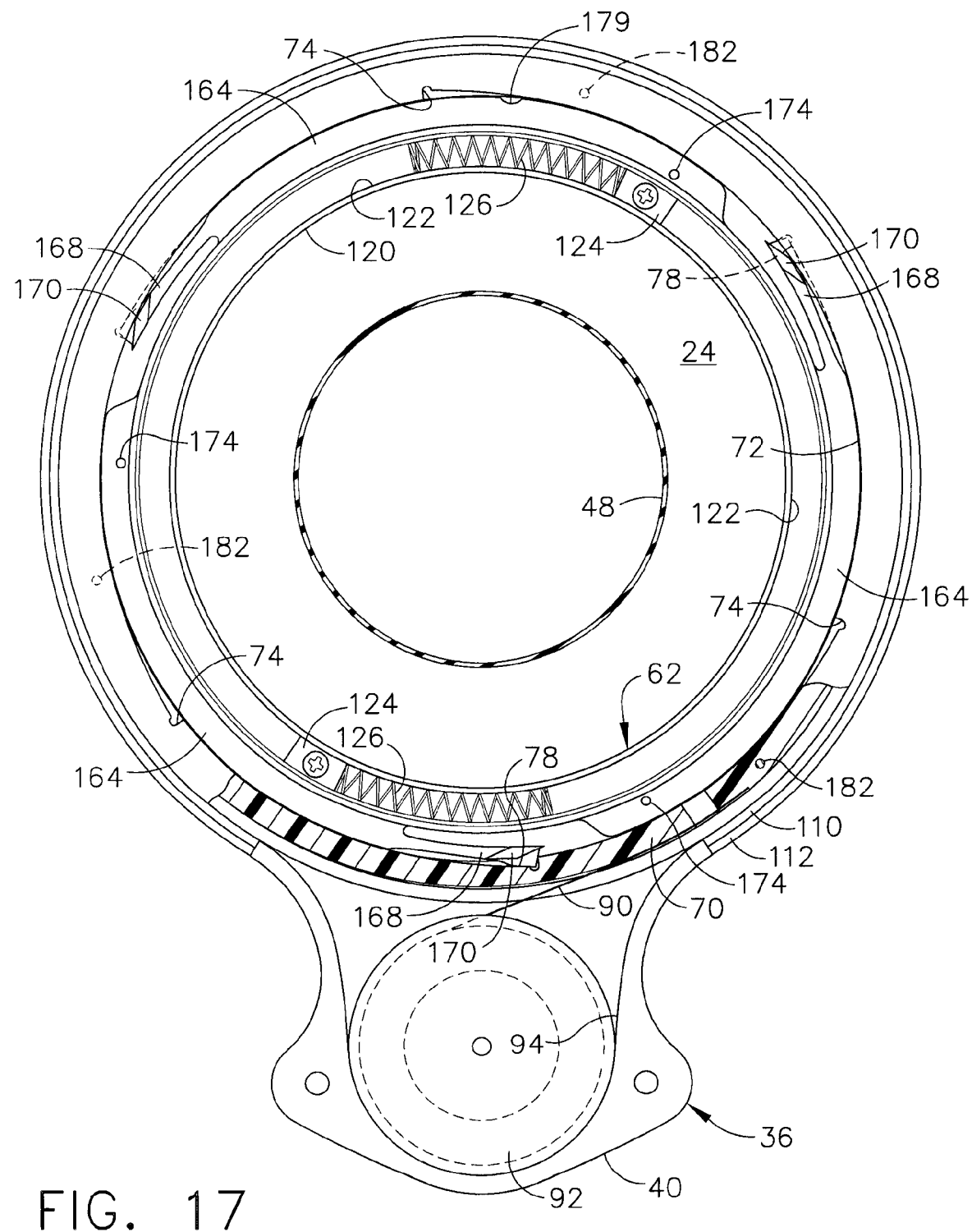
FIG. 17 is a top plan view of a bottom circumference of a tubular diaphragm twist seal and compression springs installed onto the stationary ring and a motor spring attached to the closure ring of the partially assembled laparoscopic device assembly of FIG. 16 partially cut away to expose lock arms of the stationary disk engaged to lower recesses formed in the closure disk.

In FIGS. 16-17, in addition to the closure ring 70 added in FIG. 15, the stationary ring 62 has been inserted with the motor stop arms 168 outwardly relaxed in engagement to the lower stop recesses 68 (FIG. 17) of the closure ring 70. The lower seal alignment notch 179 is positioned on an opposite side of the lower base 36 to the handle portion 40. In FIG. 17, the compression springs 126 are inserted into respective equal arcs 122 residing in contact from a counterclockwise side of a respective channel block 124. The bottom circumference 58 (FIG. 4) of the twist seal 24 has been installed onto the lower stationary ring 62 with the top circumference 48 of the twist seal 24 remaining relaxed. The motor spring 92 has also been installed upon the integral vertical spindle 96 with the tab 90 attached to the closure ring 70 to impart a clockwise bias.

Figure 18:
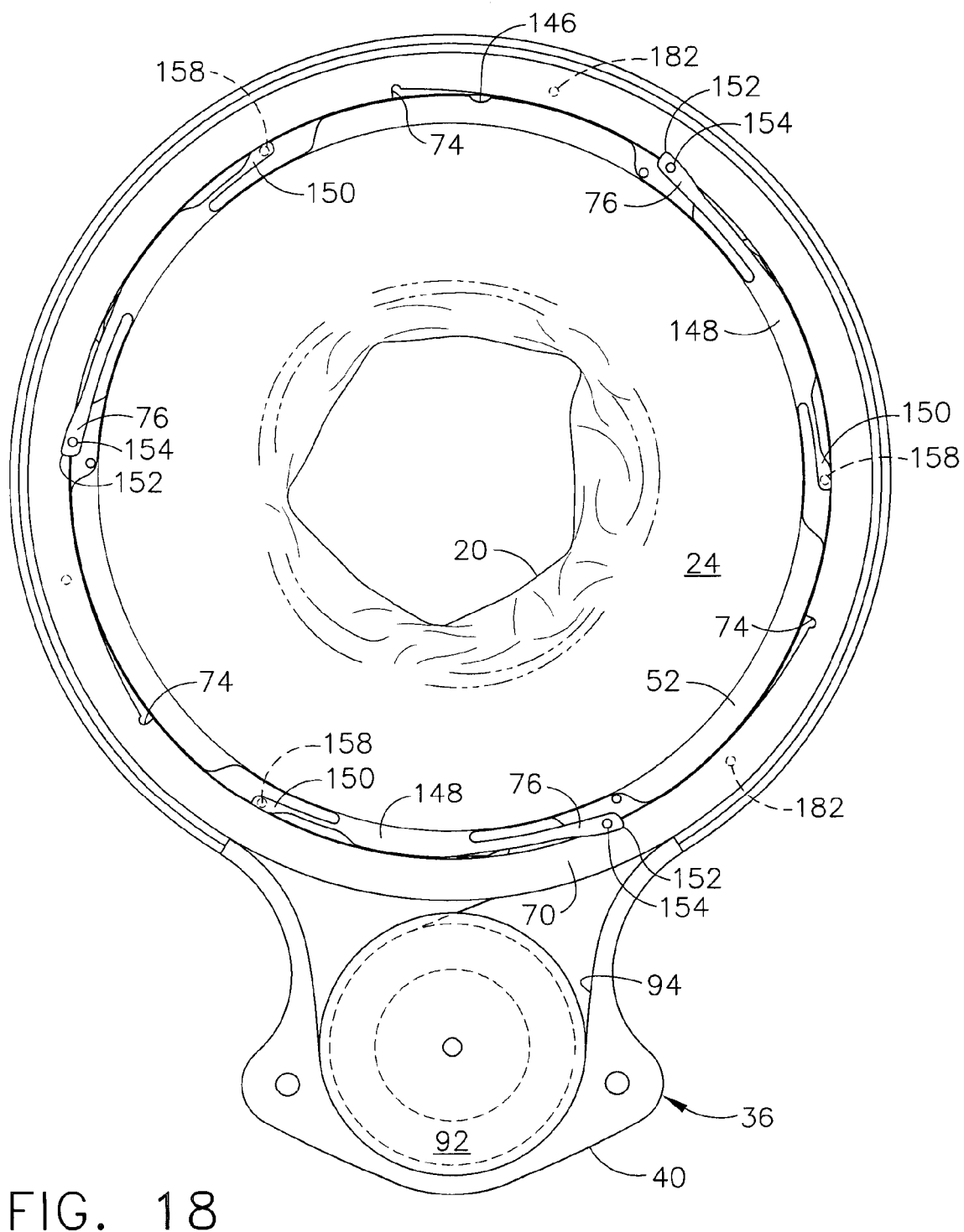
FIG. 18 is a top plan view of a top circumference of the tubular diaphragm twist seal attached to an opening ring of the partially assembled laparoscopic device assembly of FIG. 17.

In FIG. 18, the opening ring 52 has been prepared for installation with the upper seal alignment notch 146 positioned above the lower seal alignment notch 179 of the stationary ring 62 and the top circumference 48 of the twist seal 24 installed onto the opening ring 52, presenting a fully open adjustable access channel 20. The opening ring 52 has not been inserted within the inner diameter 72 of the closure ring 70 and thus the lock arms 76 of the closure ring 52 are in a relaxed, extended state above the closure ring 70.

Figure 19:
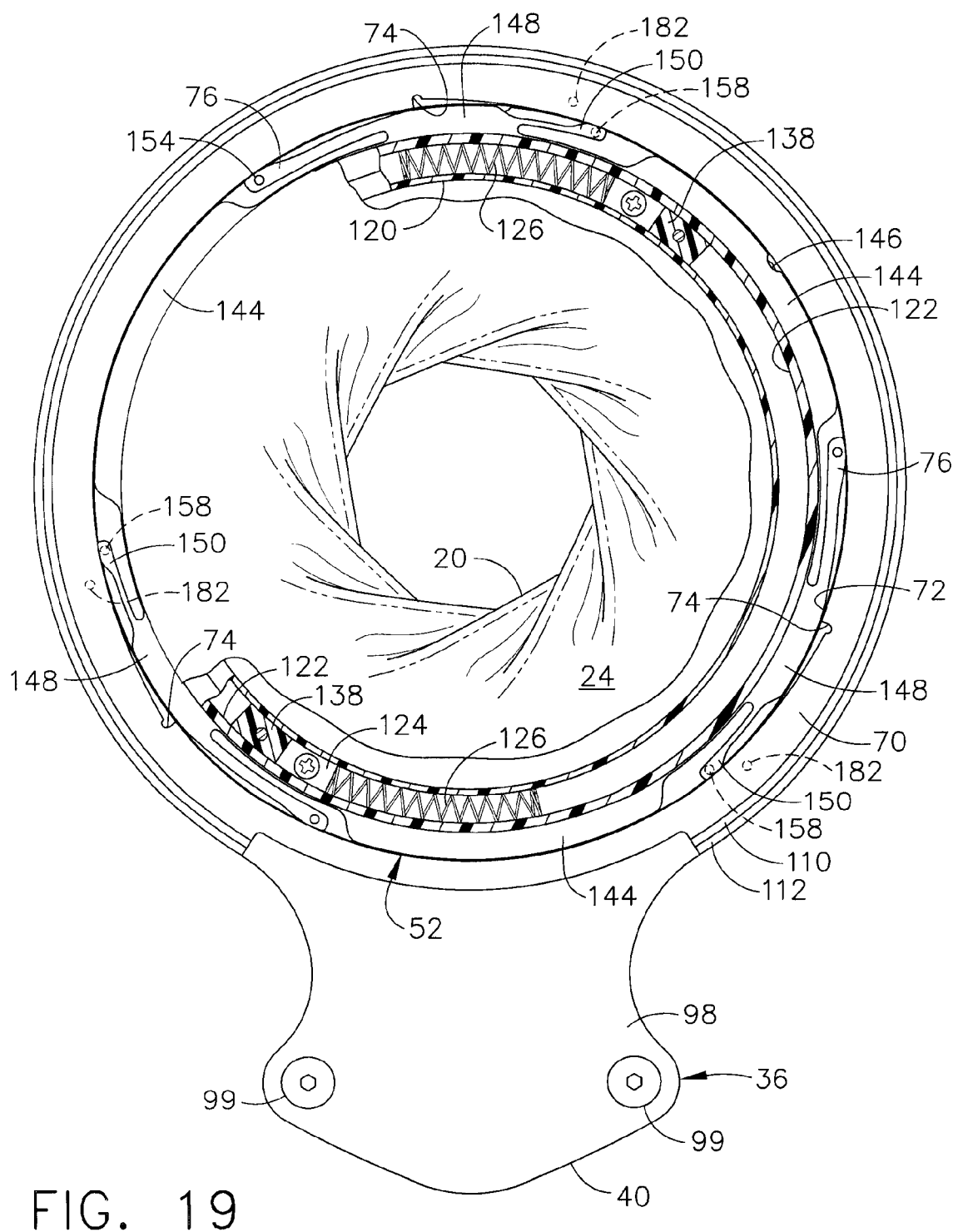
FIG. 19 is a top plan view of the partially assembled laparoscopic device assembly of FIG. 18 partially cut away to show a clockwise rotation made to the opening ring to allow spring blocks of the opening ring to drop in clockwise to channel blocks of the stationary ring as the lock arms of the opening ring are inwardly actuated by the inner diameter of the closure ring.

In FIG. 19, the opening ring 52 has been rotated clockwise less than a quarter turn until each spring block 138 of the opening ring 52 drops into a respective equal arc 122 of the spring channel 120 of the stationary ring 62 just clockwise of the respective channel blocks 124, imparting a slight twist to the adjustable access channel 20. The lock arms 76 are drawn out of the respective upper locking recesses 74 of the closure ring 70.

Figure 20:
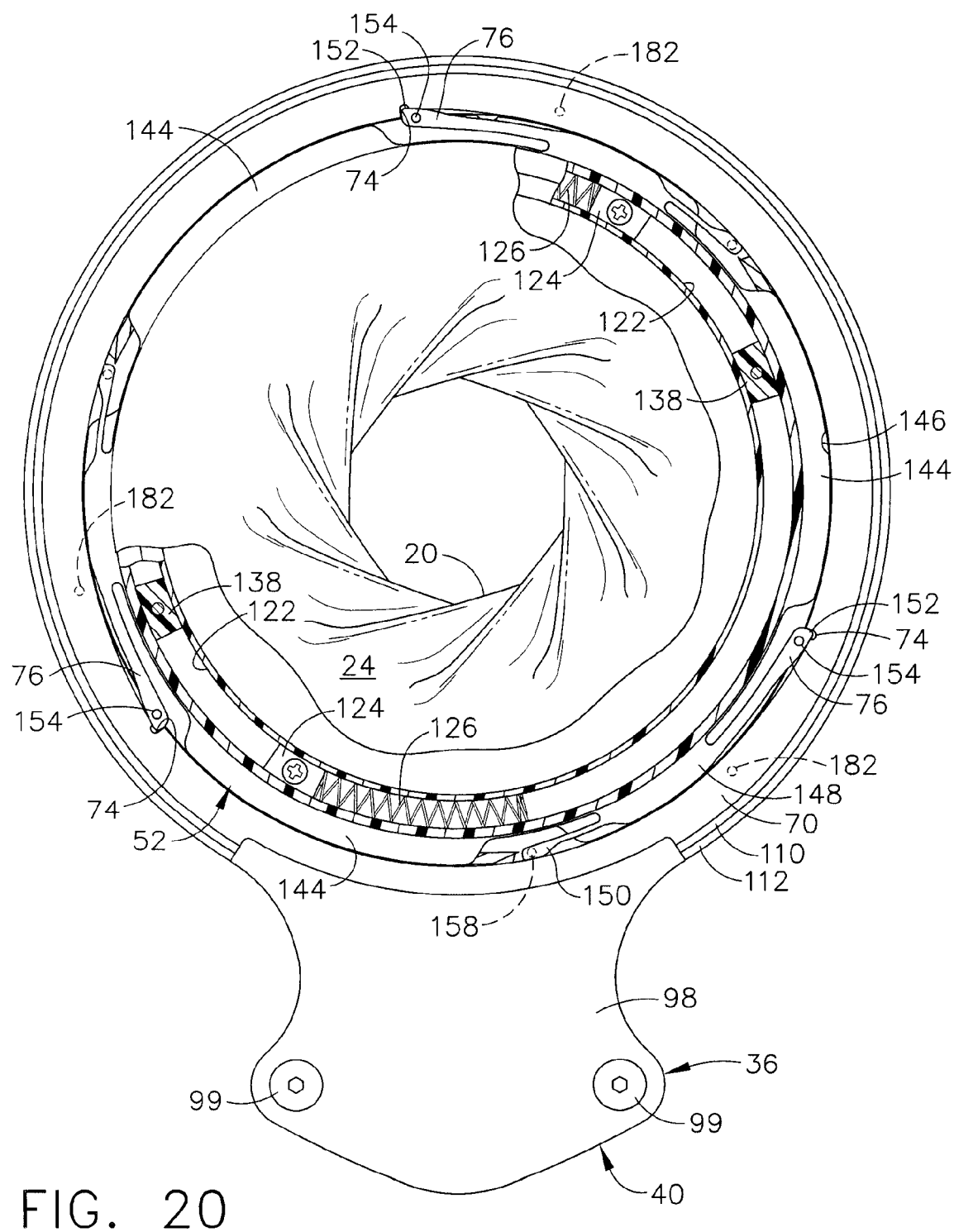
FIG. 20 is a top plan view of the partially assembled laparoscopic device assembly of FIG. 19 after further clockwise rotation of the opening ring partially cut away to show engagement of the lock arms of the opening ring within upper recesses of the closure ring.

In FIG. 20, the closure ring 52 has been further rotated clockwise, but still has not reached a quarter turn, until the lock arms 76 extend outwardly into the next encountered upper locking recesses 74 of the closure ring 70.

Figure 21:
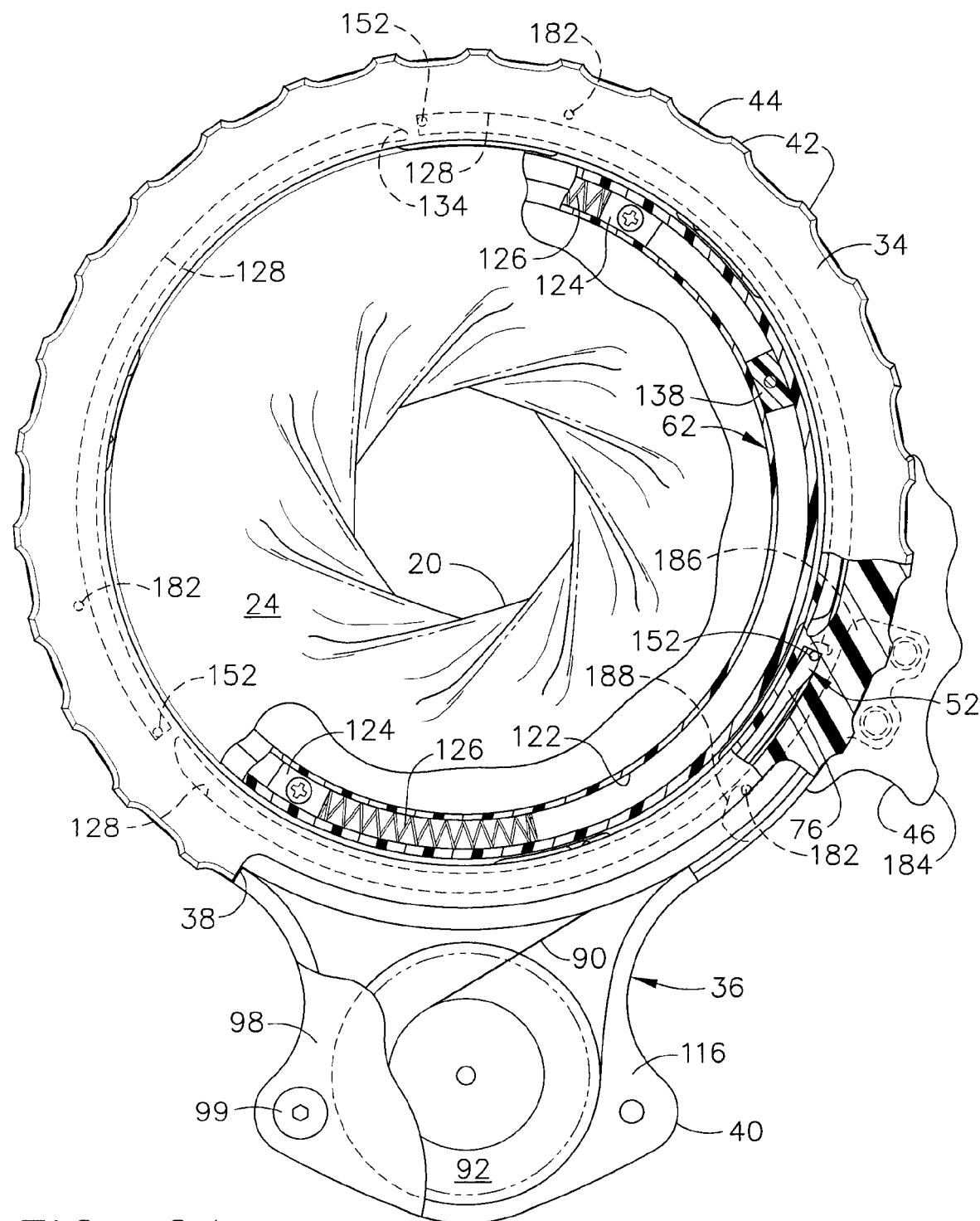
FIG. 21 is a top plan view of adding the actuating ring and the winding actuator to the partially assembled laparoscopic device assembly of FIG. 20 to complete assembly.

In FIG. 21, the handle top cover 98 has been installed. The actuating ring 34 is at its counterclockwise most position such that each upward pin 154 extending from each locking tip 152 is received within the counterclockwise termination 134 respectively of one of the three arcing grooves 128 formed in the undersurface 130 of the actuating ring 34. The winding handle 46 has been inserted into the lower base 36 and rotated counterclockwise until the hooked end 188 engages a winding pin 182 of the closure ring 70. It should be appreciated that the winding handle 46 may be detachable or permanently affixed to the laparoscopic disk 10. Thereby, one third of a counterclockwise rotation or more at a time may be imparted to the closure ring 60 to wrap the tab 90 around the spool surface 82 of the closure ring 70 to store the energy used thereafter in closing and opening the adjustable access channel 20 of the twist seal 24.

In FIG. 22, the disk assembly 10 is depicted with engagement features radially aligned in cross section, including the circular engagement lip 102 that receives the upper lip 14 of the retractor skirt 14, held in place by a bottom O-ring 196. The lock arm 76 of the opening ring 52 is extended into locking engagement with the upper recess 74 of the closure ring 70 with the upward pin 152 residing in the acing groove 128 of the actuating ring 34. The winding pin 182 extends down into the winding pin groove 192 formed in the lower base 36. The projecting pin 106, extending from the lower base 36, passes into the mounting hole 174 of the stationary ring 62 for resisting rotation. The spool surface 82 of the closure ring 70 defines an annular recess for receiving the tab 90 of the motor spring 92 (FIG. 4). The flexible ring 30 of the retractor skirt 14 is depicted as being assembled into lower opening 28, which may allow for a desired amount of rigidity.

Figure 23:
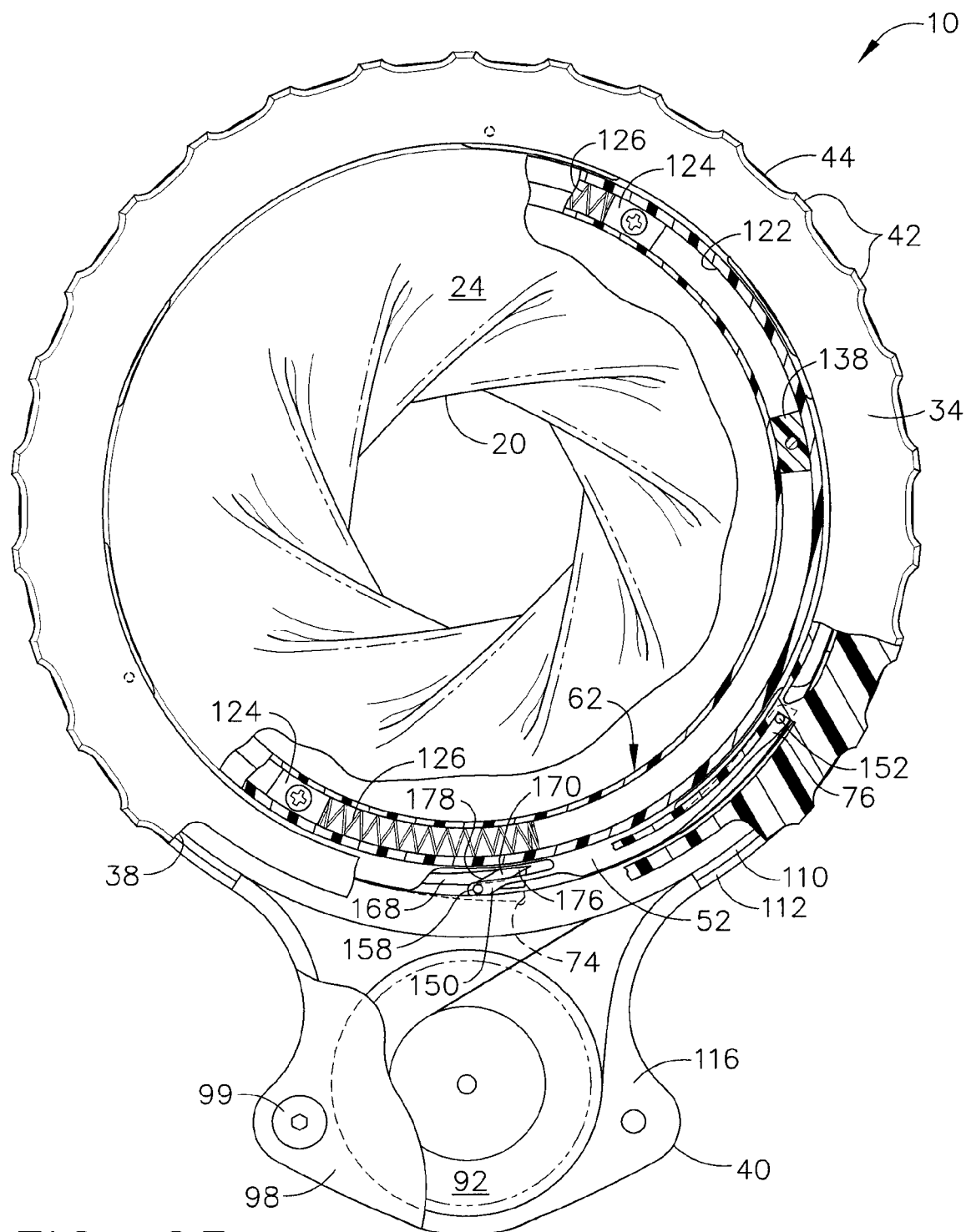
FIG. 23 is a top plan view of the assembled laparoscopic device assembly of FIG. 21 after a clockwise rotation of the actuating ring partially cut away to expose the clockwise rotation of the opening ring releasing motor stop arms of the stationary ring to release the closure ring for clockwise rotation.

In FIG. 23, the actuating ring 34 is being turned clockwise such that the counterclockwise termination arcing grooves 128 impart a clockwise rotation to the upward pins 152 of the opening ring 52, with the lock arms 76 being pulled out of any encountered upper recesses 74 of the closure ring 70 that may otherwise impede clockwise rotation of the closure ring 70. Each release arm 150 of the opening ring 52 presents the downward pin 158 that encounters the distal ramped surface 176 of the bypass key 170 of the respective motor stop arm 168 of the stationary ring 62, urging the motor stop arm 168 inwardly out of engagement with the respective lower recess 78 of the closure ring 70 (FIG. 4).

Figure 24:
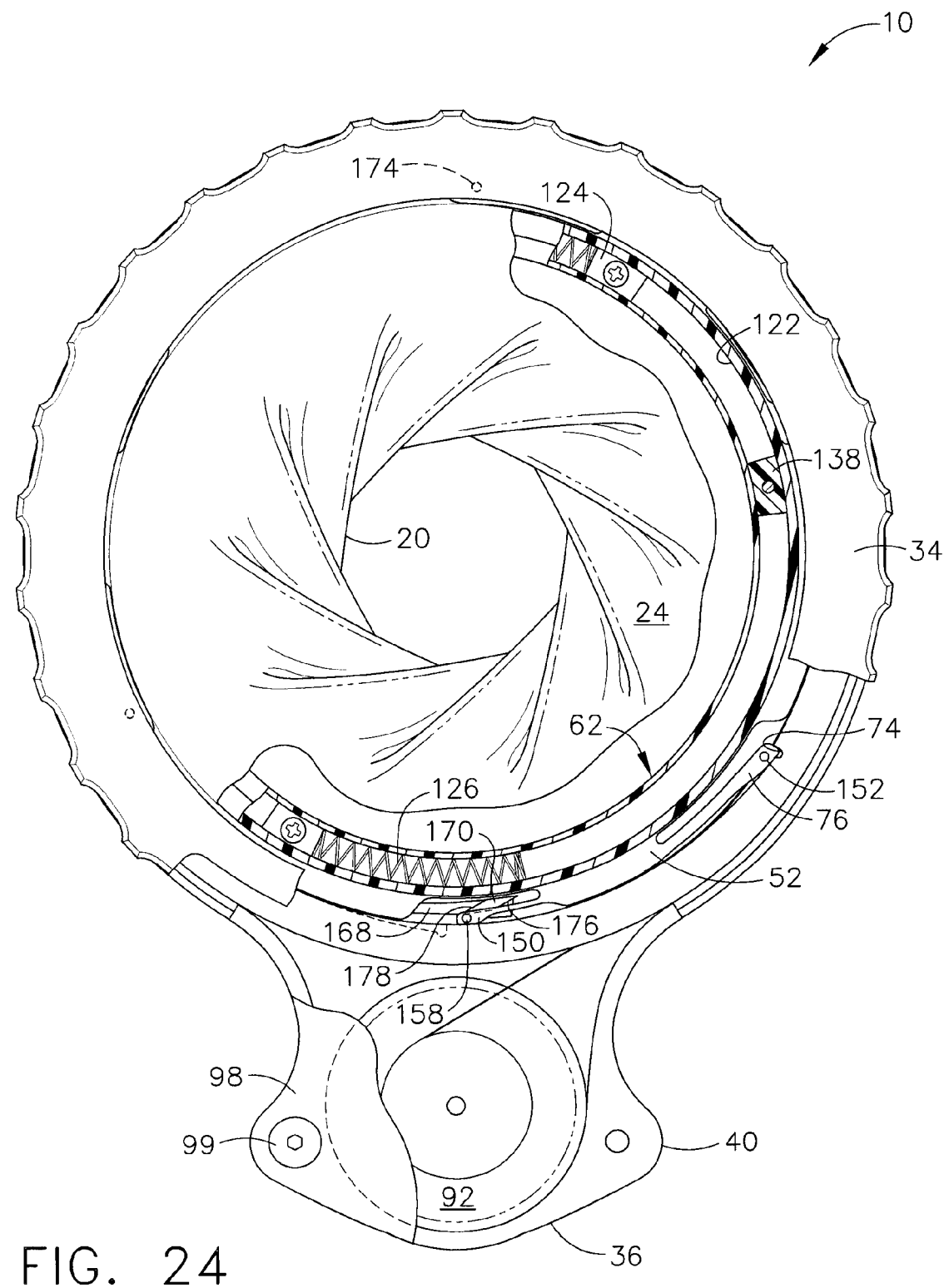
FIG. 24 is a top plan view of the assembled laparoscopic device assembly of FIG. 23 as the closure ring begins clockwise rotation and engages the lock arms of the opening ring.
Figure 25:
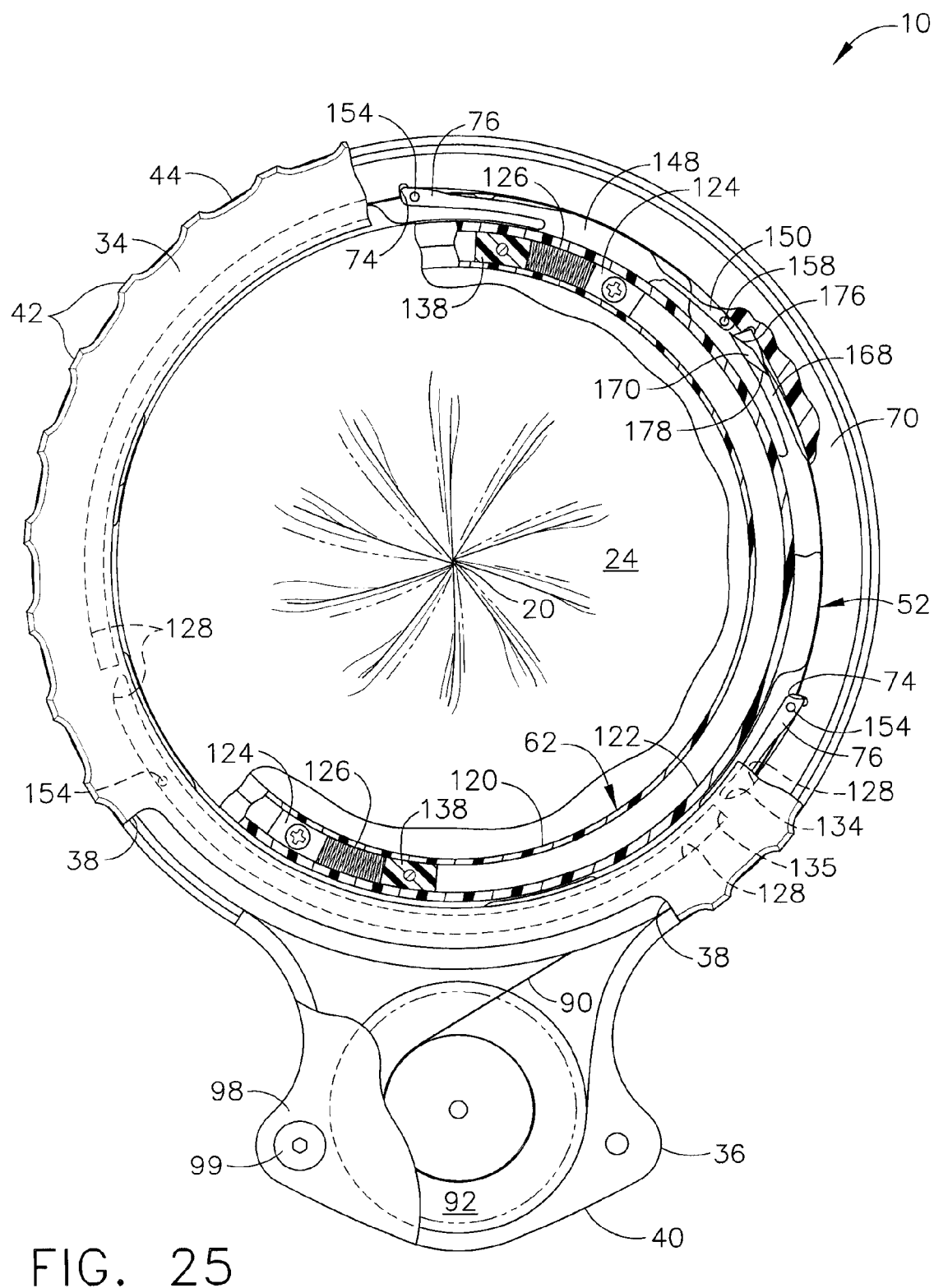
FIG. 25 is a top plan view of the assembled laparoscopic device assembly of FIG. 24 after the closure ring has full clockwise rotated, closing the twist seal and partially cut away to show the compressing of the compression springs between the spring blocks of the opening ring and the channel blocks of the stationary ring and the maintained engagement of the lock arms to the closure ring.

In FIG. 24, with the closure ring 70 released from being blocked for clockwise rotation by both the opening and stationary rings 52, 62, the stored energy of the motor spring 92 begins to rotate the closure ring 70, which almost immediately results in the lock arms 76 reengaging the upper recesses 74 of the closure ring 70. The upper pins 152 of the opening ring 52 do not impede the clockwise rotation of the opening ring 52 relative to the actuating ring 34 for the angular dimension of the respective arcing groove 128 of the actuating ring. Thus, in FIG. 25, the motor spring 92 rotates both the opening ring 52 and the closure ring 70 for approximately 30° one third of a rotation until the spring blocks 138 of the opening ring compress the respective compression spring 126 against the channel block 124 of the stationary ring 62, and thus impart a like additional twist of the bottom circumference 58 of the twist seal 24 relative to the top circumference 48, closing the adjustable access channel 20 to form a pneumatic seal. The upward pins 152 of the opening ring 52 are approaching the respective clockwise terminations 134 of the arcing grooves 128, and have not yet been drawn inwardly but instead remain in the extended, locking condition.

Figure 26:
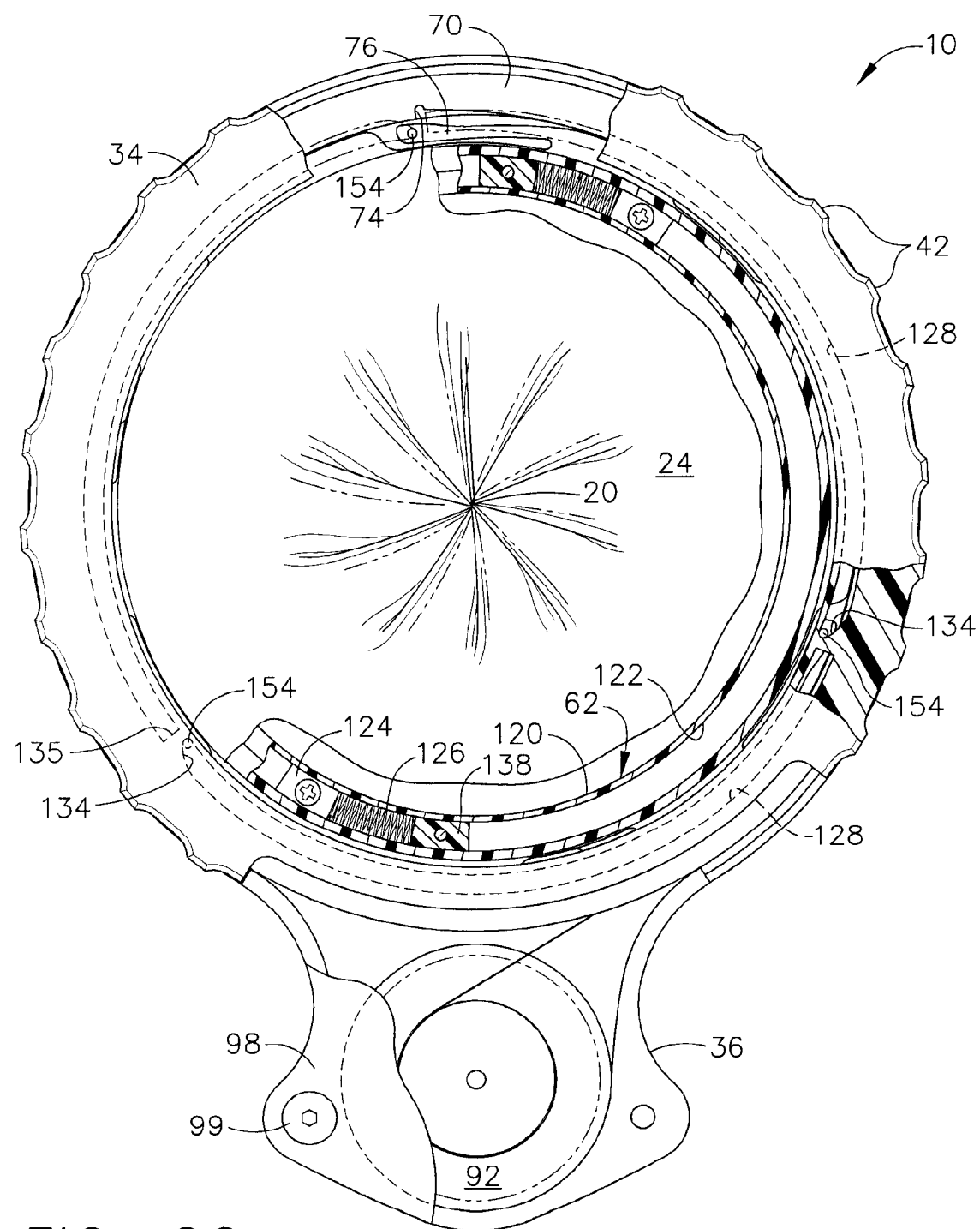
FIG. 26 is a top plan view of the assembled laparoscopic device assembly of FIG. 25 after the actuating ring has been rotated clockwise partially cut away to expose the upper pins of the opening ring entering the clockwise terminations of the arcing grooves in the actuating ring that inwardly draw the lock arms out of engagement with the closure ring.

In FIG. 26, the user has rotated the actuating ring 34 counterclockwise the amount allowed by the small outer portion 38 about the handle portion 40, causing the clockwise termination 134 of the arcing groove 128 of the actuating ring 34 to present an inwardly ramping motion upon the respective upward pins 152 from the opening ring 52, drawing the attached lock arms 76 inwardly out of engagement with the closure ring 70. The compression springs 126 and the full twisted state of the adjustable access channel 20 of the twist seal 24 both impart a counterclockwise urging upon the opening ring 52.

Figure 27:
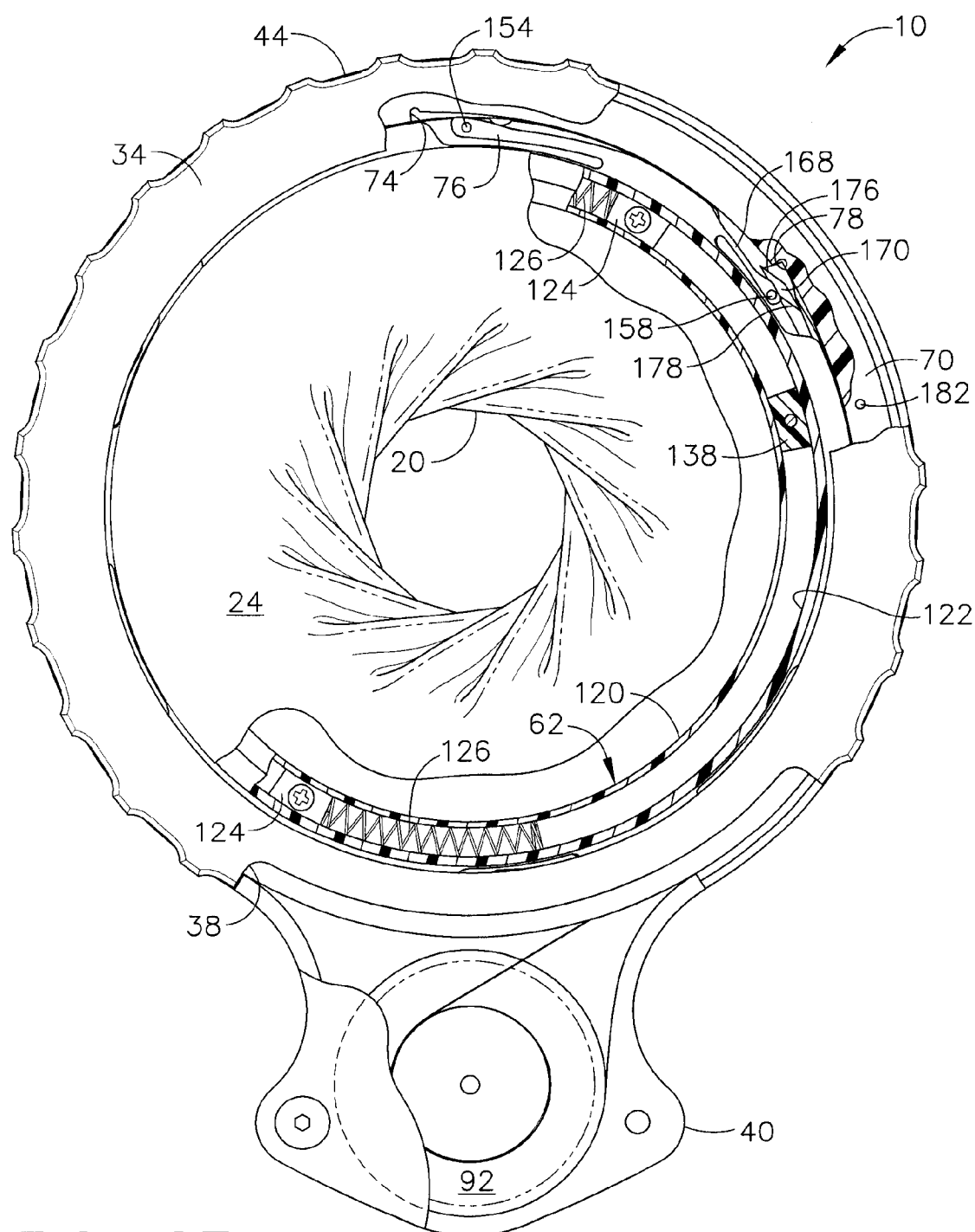
FIG. 27 is a top plan view of the assembled laparoscopic device assembly of FIG. 26 as the stored energy of the compression spring and the fully closed twist seal are being leased into the opening ring as a counterclockwise rotation.

In FIG. 27, the opening ring 52 has begun to respond to this counterclockwise urging, releasing the compression springs 126 and allowing the twist seal 24 to open as the top circumference 48 rotates counterclockwise. The downward pin 158 of each release arm 150 of the opening ring 52 encounters the opposite ramping surface 178 of the bypass key 170 of the motor stop arms 168 of the stationary ring 62 and is urged inwardly, allowing the motor stop arms 168 to remain engaged within the lower recess 78 of the closure ring 70.

Figure 28:
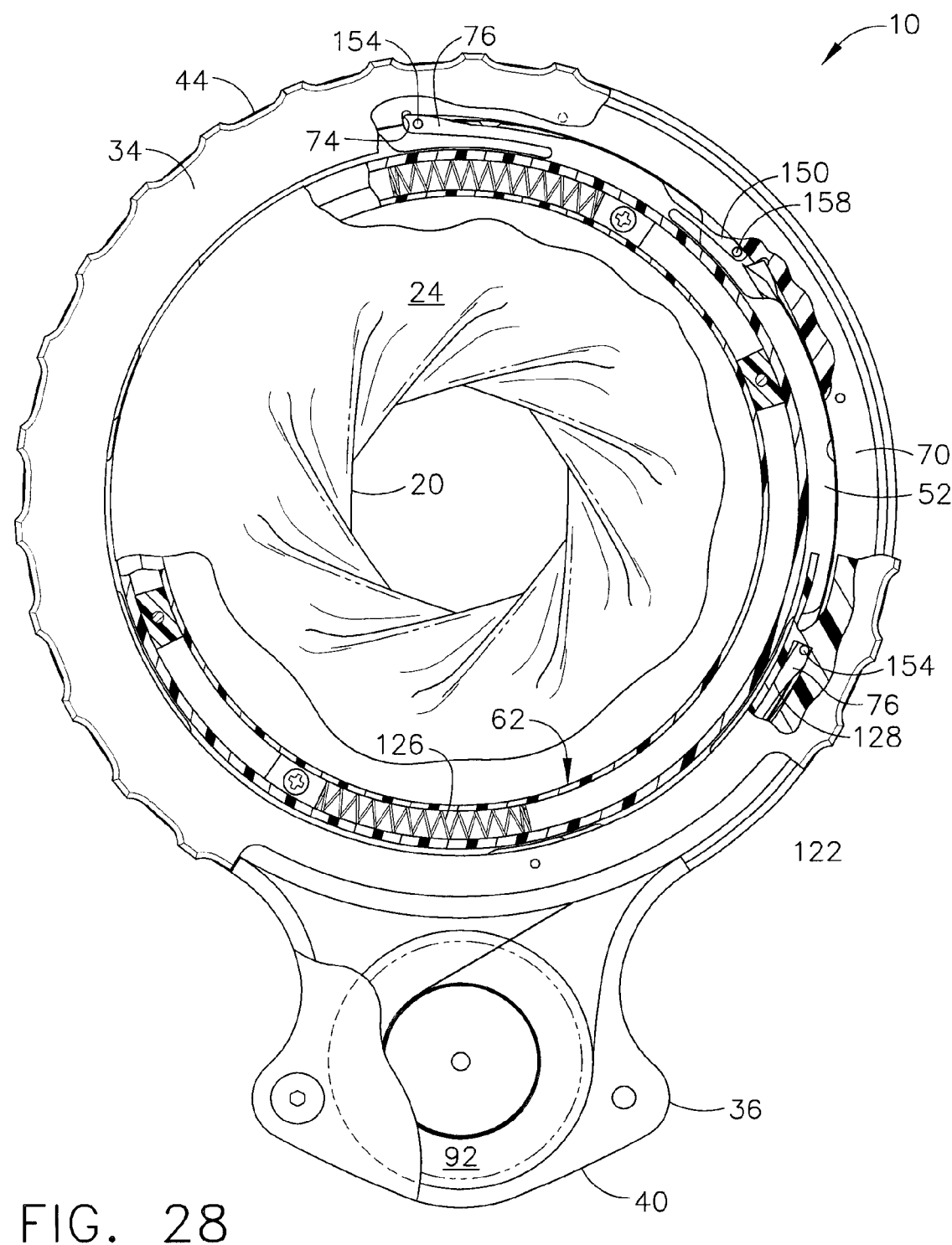
FIG. 28 is a top plan view of the assembled laparoscopic device assembly of FIG. 27 after the opening ring completes the counterclockwise rotation so that the lock arms engage the next respective upper recesses in the closure ring, presenting an open condition of the twist seal.

In FIG. 28, the opening ring 52 has been fully rotated counterclockwise such that each lock arm 76 is allowed to engage the next encountered upper recess 74 of the closure ring 70, preparing the laparoscopic device assembly 10 for the insertion of the surgeon's hand. The amount of biasing for closing and opening may be selected as approximate to achieve the desired amount of opening and closing at an appropriate rate, overcoming friction and resiliency characteristics of the twist seal 24. Rapid closing (e.g., two seconds or less) is deemed efficacious to reduce pneumatic pressure loss.

Figure 29:
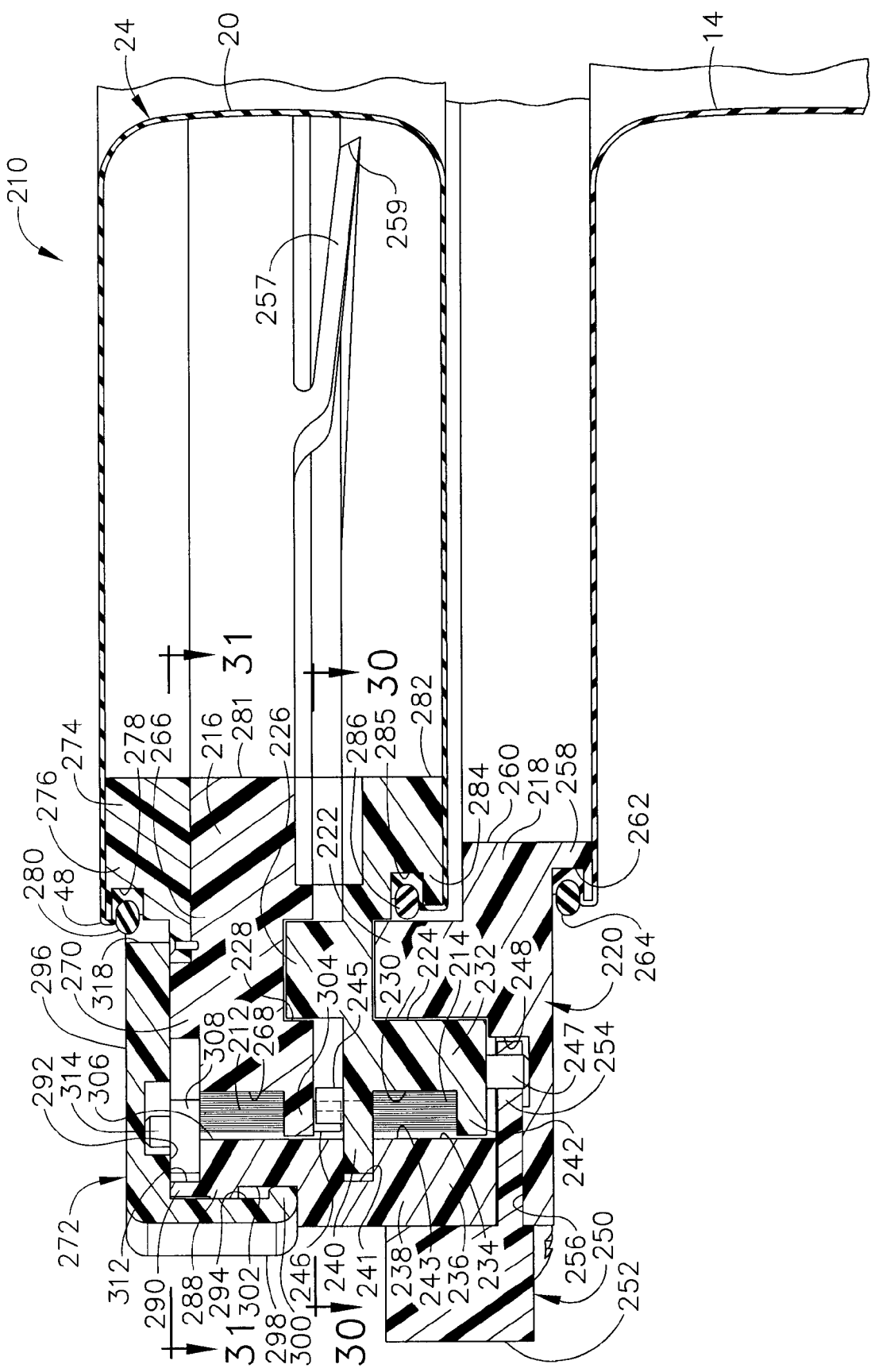
FIG. 29 is a side view in vertical cross section through an alternative laparoscopic disk assembly.

In FIGS. 29-35, an alternate HALS laparoscopic disk assembly 210 incorporates two biasing springs, depicted as an upper motor spring 212 and a lower motor spring 214 that bias respectively an opening ring 216 and a closure ring 218 for independent movement in the same selected direction relative to an encompassing lower housing 220 for opening and closing. With particular reference to FIG. 29, a cylindrical lower bearing rail 222 of the lower housing 220 extends upwardly within a downwardly open cylindrical recess 224 formed in the closure ring 218. In turn, a cylindrical upper bearing rail 226 of the closure rail 218 that is vertically aligned with the lower bearing rail 222 extends upwardly into a downwardly open cylindrical recess 228 formed in the opening ring 216. These engagements constrain the rotational movement of the rings 216, 218 relative to the housing 220.

An outward bobbin recess 230 formed outward from a downward cylindrical portion 232 of the closure ring 216 surrounding the lower bearing rail 226 forms a lower annular cavity 234 with a lower portion 236 of an upwardly projecting outer cylindrical wall 238 of the lower housing 220 for wrapping the lower motor spring 214 around the closure ring 218.

Figure 30:
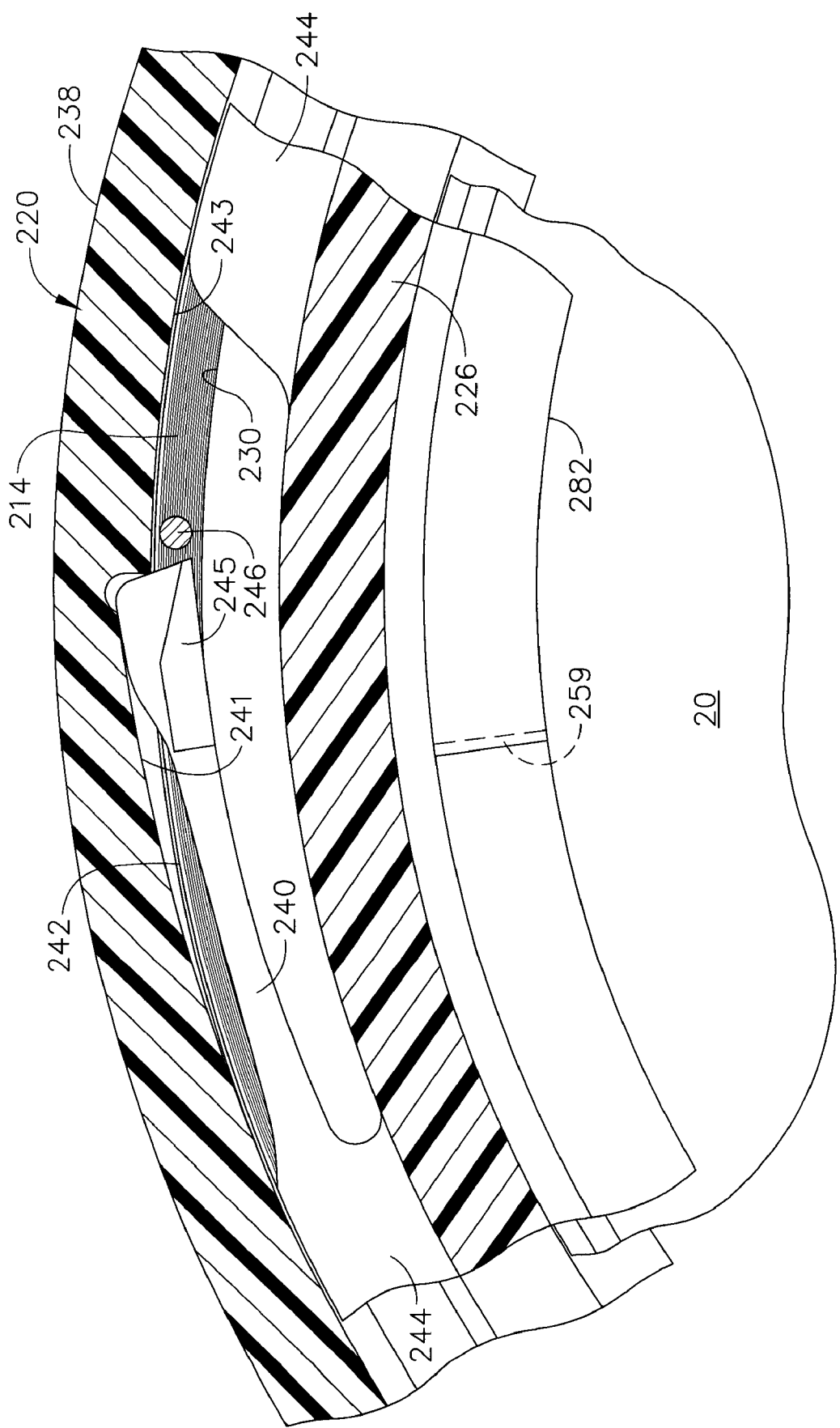
FIG. 30 is a top detail view of the alternative laparoscopic disk assembly of FIG. 29 horizontally cut away to show a closure lock arm of a closure ring engaged to a lower ratchet recess of a lower housing.

In FIGS. 29-30, a closure lock arm 240 of the closure ring 218 resiliently extends outwardly received within a lower ratcheting recess 241 formed in the lower portion 236 of the lower housing 220. A lower lip 242 contacts for rotational movement an inner diameter 243 of the upwardly projecting outer cylindrical wall 238 of the lower housing 220 and defines the lower limit of the bobbin recess 230. In FIG. 30, an interrupted upper circumferential lip 244 of the closure ring 218 circumferentially brackets the one or more closure lock arms 240 for contacting for rotational movement the inner diameter 243 of the outer cylindrical wall 238 and defines the upper limit of the bobbin recess 230. The closure lock arm 240 extends clockwise tending to abut a clockwise termination of the lower ratcheting recess 241, preventing further clockwise rotation of the closure ring 218. In FIGS. 29-30, the closure lock arm 240 upwardly presents a closing key 245 profiled to contact an inner side of a downward lower actuation pin 246 extending down from the opening ring 216. Thus, a counterclockwise moving opening ring 216 unlocks the closure ring 218.

Winding pins 247 extend downwardly from the downward cylindrical portion 232 of the closure ring 218 within an upwardly open annular winding pin recess 248 formed in the lower housing 220 outward from the lower bearing rail 222. A winding actuator 250 presents an external handle 252 with an internal hook 254 extending inwardly for rotation within a horizontal winding slot 256 formed through the lower portion 236 of the lower housing 220 to engage and move a respective winding pin 247. At least one winding ratchet arm 257 extends downwardly and clockwise from the opening ring 216 and is received in a counterclockwise upwardly ramped recess 259 formed on an upper surface of the closure ring 218. Thus counterclockwise winding rotation of the closure ring 218 is communicated also to the opening ring 216.

A downwardly projecting circular engagement lip 258 of the lower housing 220 surrounding an inner diameter 260 of the lower housing 220 has an outwardly open annular recess 262 that receives the upper lip 14 of the retractor skirt 14, held in place by a bottom O-ring 264.

The opening ring 216 is assembled from a lower disk portion 266 that has an outwardly open bobbin surface 268 and an upwardly cylindrical guide rail 270 that rotates again an actuating ring 272. An upper disk portion 274 of the opening ring 216 has an upper lip 276 with an outwardly open annular recess 278 that receives the top circumference 48 of the twist seal 24 and is held there by a top O-ring 280. The adjustable access channel 20 of the twist seal 24 passes through an inner diameter 281 of the opening ring 216 and an inner diameter 282 of the closure ring 218 with a bottom circumference 58 of the twist seal 24 downwardly stretched and curled outwardly and over a downwardly defined lower circular lip 284 and into an outwardly open annular recess 285 on the closure ring 218, held thereon by a lower O-ring 286. The upper disk portion 274 may be fastened to the lower disk portion 266 at a selected relative angular orientation, facilitating assembly with a proper angular pre-set of the twist seal 24.

An upper portion 288 of the upwardly projecting outer cylindrical wall 238 includes an upper and outer cylinder edge 290 that contacts both a horizontal inner surface 292 and a vertical inner surface 294 of the actuating ring 272 at the circular attachment between a horizontal disk portion 296 and a downward cylindrical band 298 of the actuating ring 272. The downward cylindrical band 298 terminates in an inward gripping lip 300 that snaps into an outwardly open annular recess 302 formed in the upper portion 288 below the outer guide lip 290.

Figure 31:
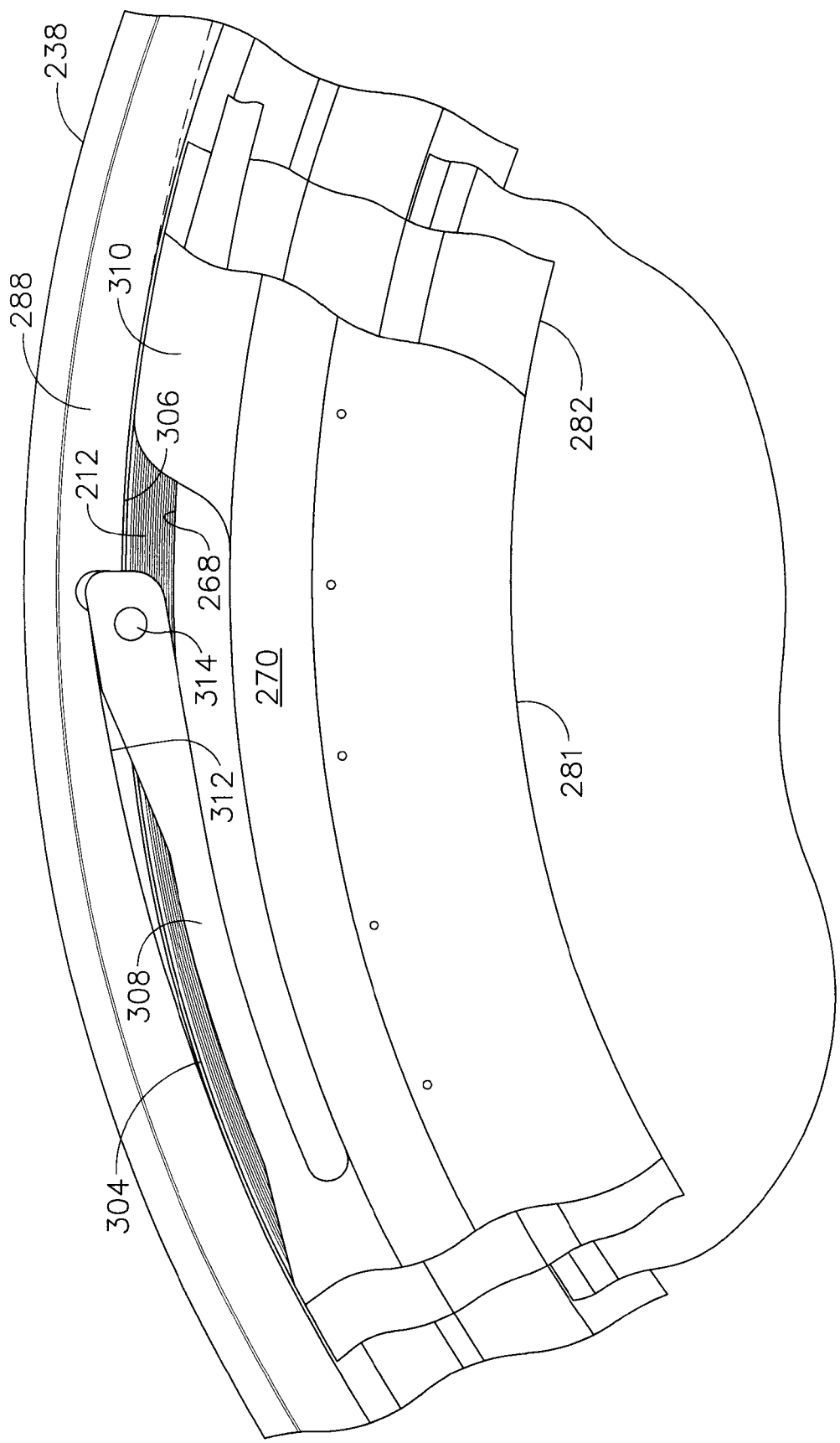
FIG. 31 is a top detail view of the alternative laparoscopic disk assembly of FIG. 29 partially disassembled to show an opening lock arm of an opening ring engaged to an upper ratchet recess of a lower housing.
Figure 33:
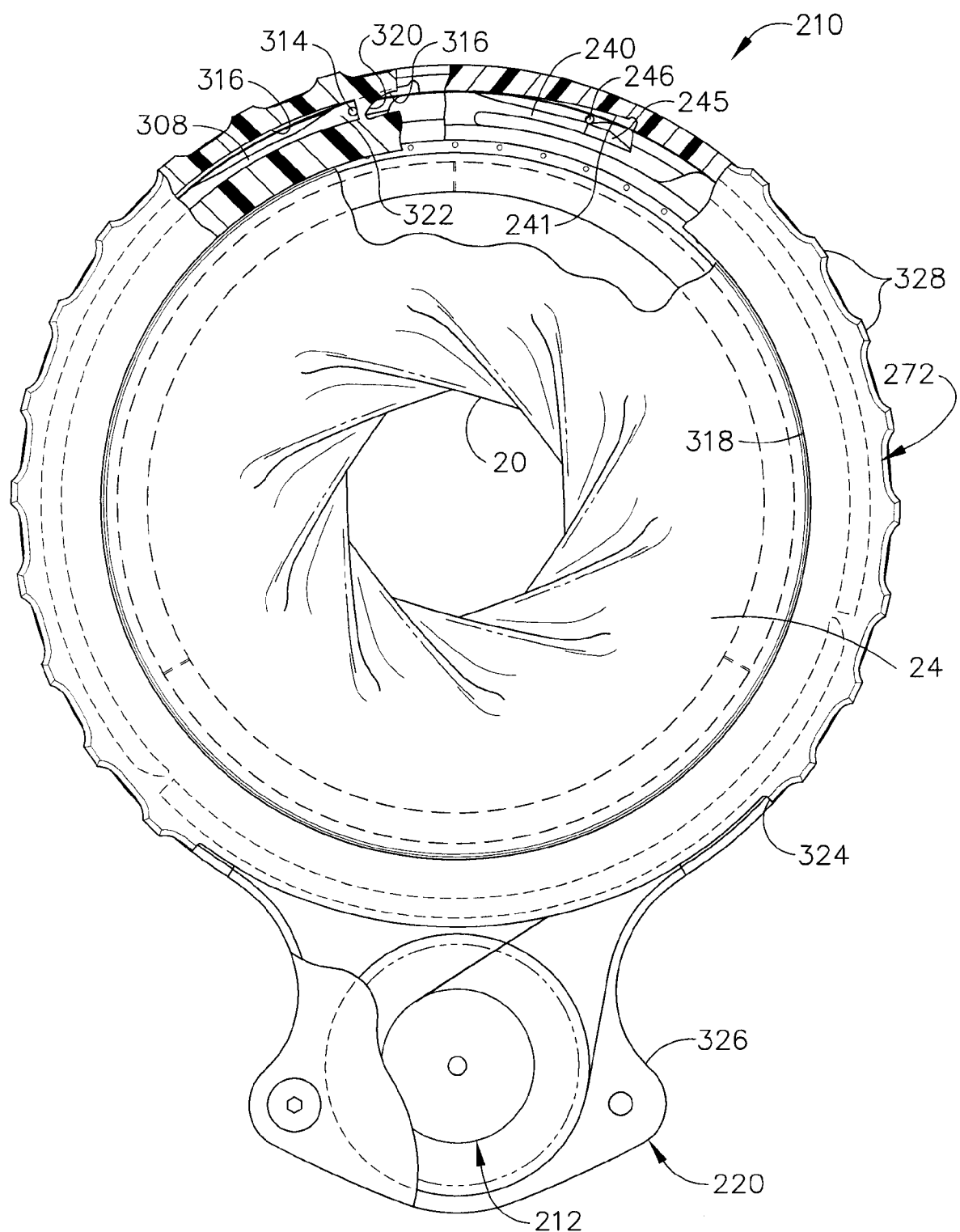
FIG. 33 is a top view of the alternative laparoscopic disk assembly of FIG. 32 partially cut away to expose the closure and opening lock arms as an actuating ring is rotated counterclockwise to disengage the closure lock arm from the lower housing.

In FIGS. 29 and 31, the lower disk portion 266 of the opening ring 216 includes a lower lip 304 that contacts for rotational movement an inner diameter 306 of the upper portion 288 of the outer cylindrical wall 238 and defines a lower limit of the bobbin surface 268 of the opening ring 216. At least one opening lock arm 308 radially bracketed by an interrupted upper circumferential lip 310 defines an upper limit of the bobbin surface 268. The interrupted upper circumferential lip 310 contacts for rotational movement inner diameter 306. The opening lock arm 308 extends clockwise and is resiliently biased outwardly to engage a clockwise termination of an upper ratcheting recess 312 formed into an inner and upper portion of the inner diameter 306, preventing further clockwise rotation of the opening ring 216. An upper actuation pin 314 extends upwardly from the opening lock arm 308 to move within one of three downwardly presented arcing grooves 316 formed on the actuating ring 272 circumscribing a portion of a central large hole 318 of the actuating ring 272 that in turn surrounds the upper disk portion 274 of the opening ring 216. In FIG. 33, each counterclockwise termination 320 (as viewed in cutaway from above) of each arcing groove 316 narrows by receding inwardly to a point and each clockwise termination 322 of the respective arcing groove 316 ends in a squared off fashion. Thus, a clockwise moving actuating ring 272 with the upper actuation pin 314 entering the counterclockwise termination 320 pulls inwardly the opening lock arm 308 out of engagement with the upper ratcheting recess 312.

Figure 32:
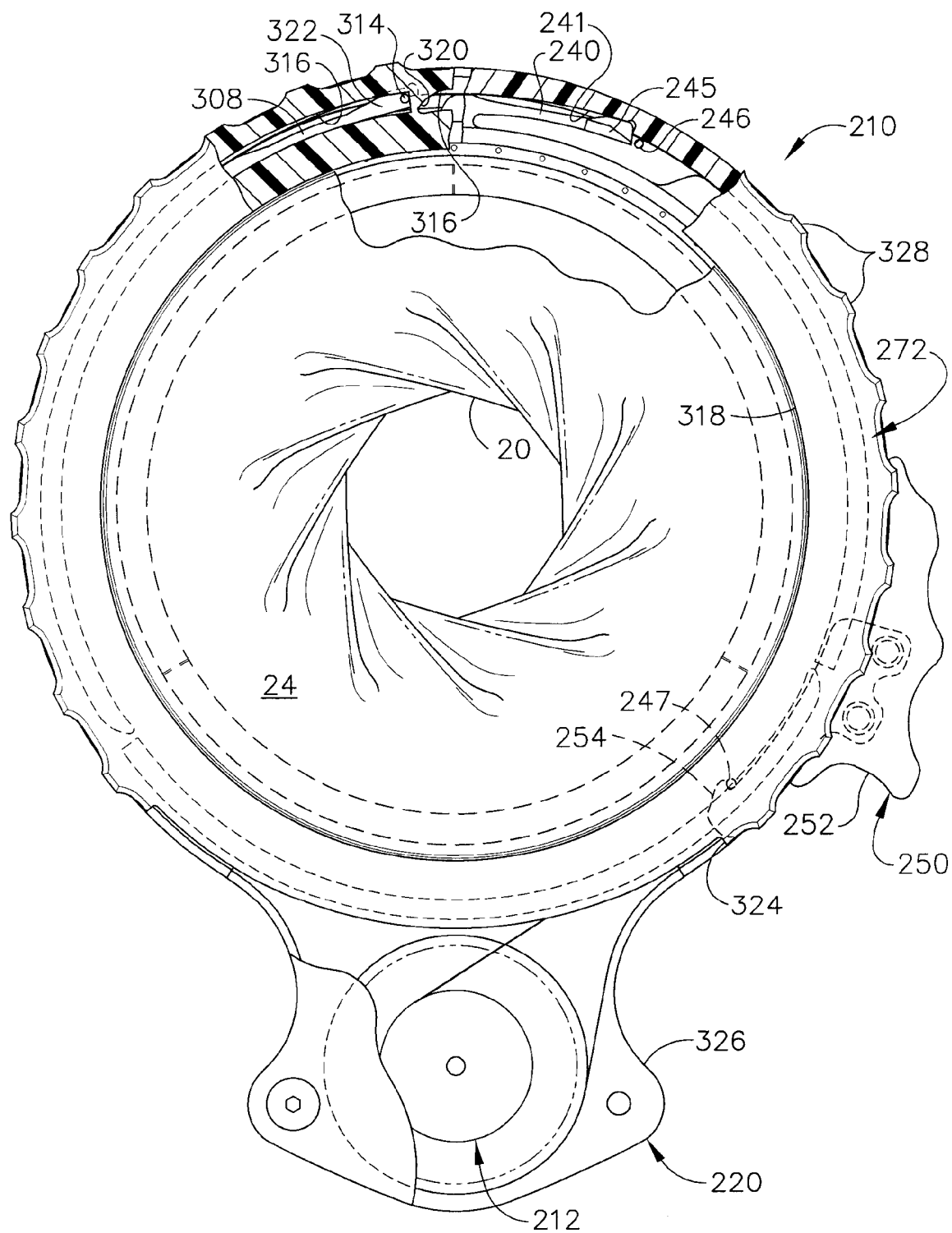
FIG. 32 is a top view of the alternative laparoscopic disk assembly of FIG. 29 in an initial open state partially cut away to expose the closure and opening lock arms engaged to the lower housing.

In FIG. 32, the laparoscopic disk assembly 210 is depicted with the adjustable access channel 20 defined by the amount of twist of the tubular diaphragm twist seal 24 in an open state. The opening lock arm 308 is engaged to the upper ratcheting recess 312 with the upper actuating pin 314 residing within the clockwise termination 322 of the arcing groove 316 of the actuating ring 272. A small outer portion 324 of the upper actuating ring 272 is cut away to allow this rotation to each side of a handle portion 326 of the lower housing 220. In FIG. 32, the small outer portion is rotated to a clockwise position with a larger opening to the left of the handle portion 326. Finger ridges 328 about a larger outer portion 330 of the upper actuating ring 272 enhance single hand operation when the palm grasps the handle portion 326. The closing lock arm 240 of the closure ring 218 is engaged to the lower ratcheting recess 241 with the closing key 245 just counterclockwise to the lower actuation pin 246 of the opening ring 216.

Figure 34:
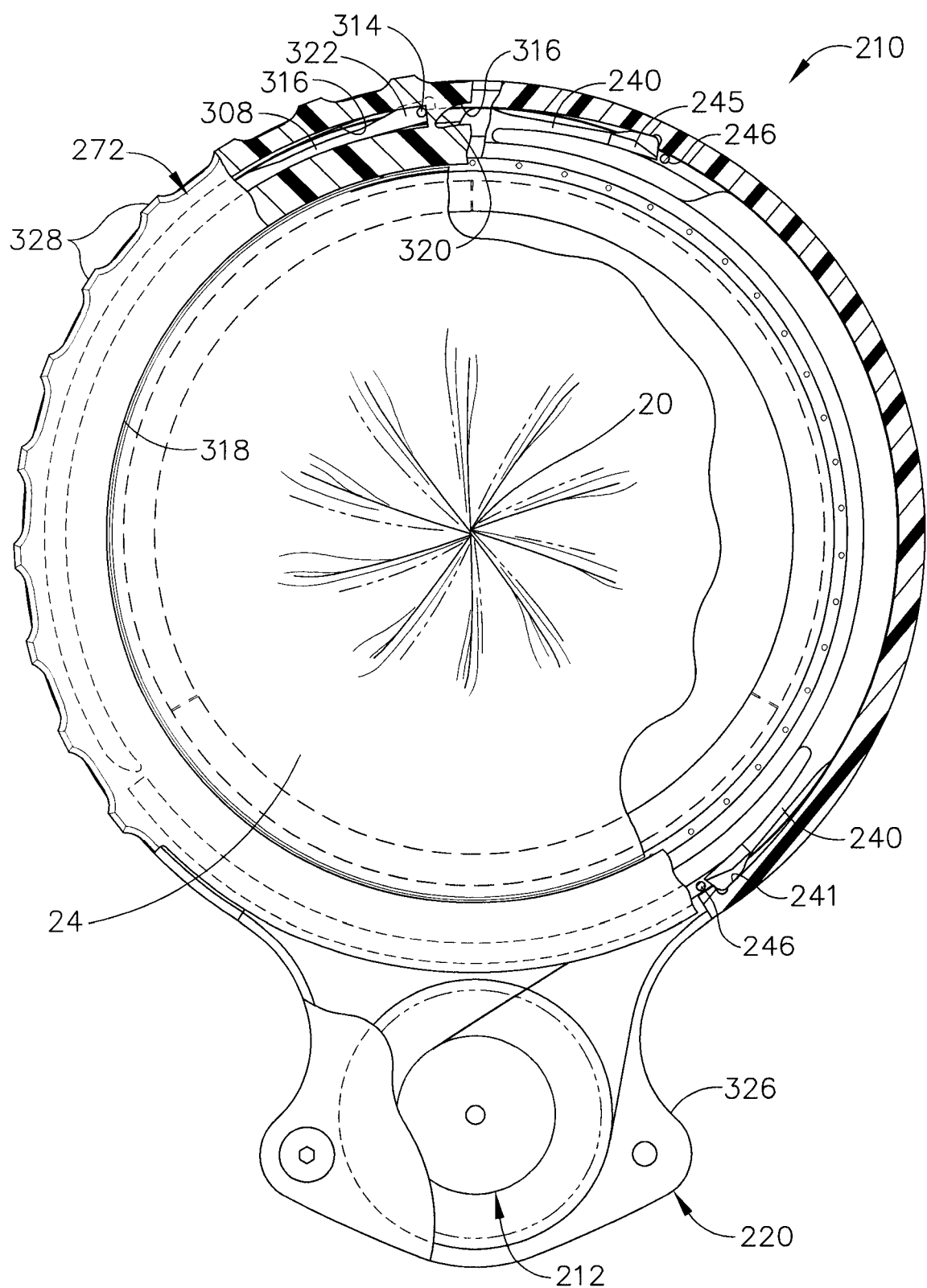
FIG. 34 is a top view of the alternative laparoscopic disk assembly of FIG. 33 partially cut away to expose the disengaged closure ring rotating clockwise one third of a rotation to reengage the lower housing at the next lower ratchet recess location.

In FIG. 33, the actuating ring 272 has been rotated counterclockwise. The arcing groove 316 has pulled the upper actuating pin 314 counterclockwise, rotating the opening ring 216 counterclockwise. Thereby, the lower actuation pin 246 ramps against the closing key 245, pulling the closure lock arm 240 out of the lower ratchet recess 241, releasing the closure ring 218 to rotate approximately one third of a clockwise rotation under the urging of the lower motor spring 214 until the closure lock arm 240 engages the next lower ratchet recesses 241, as depicted in FIG. 34.

Figure 35:
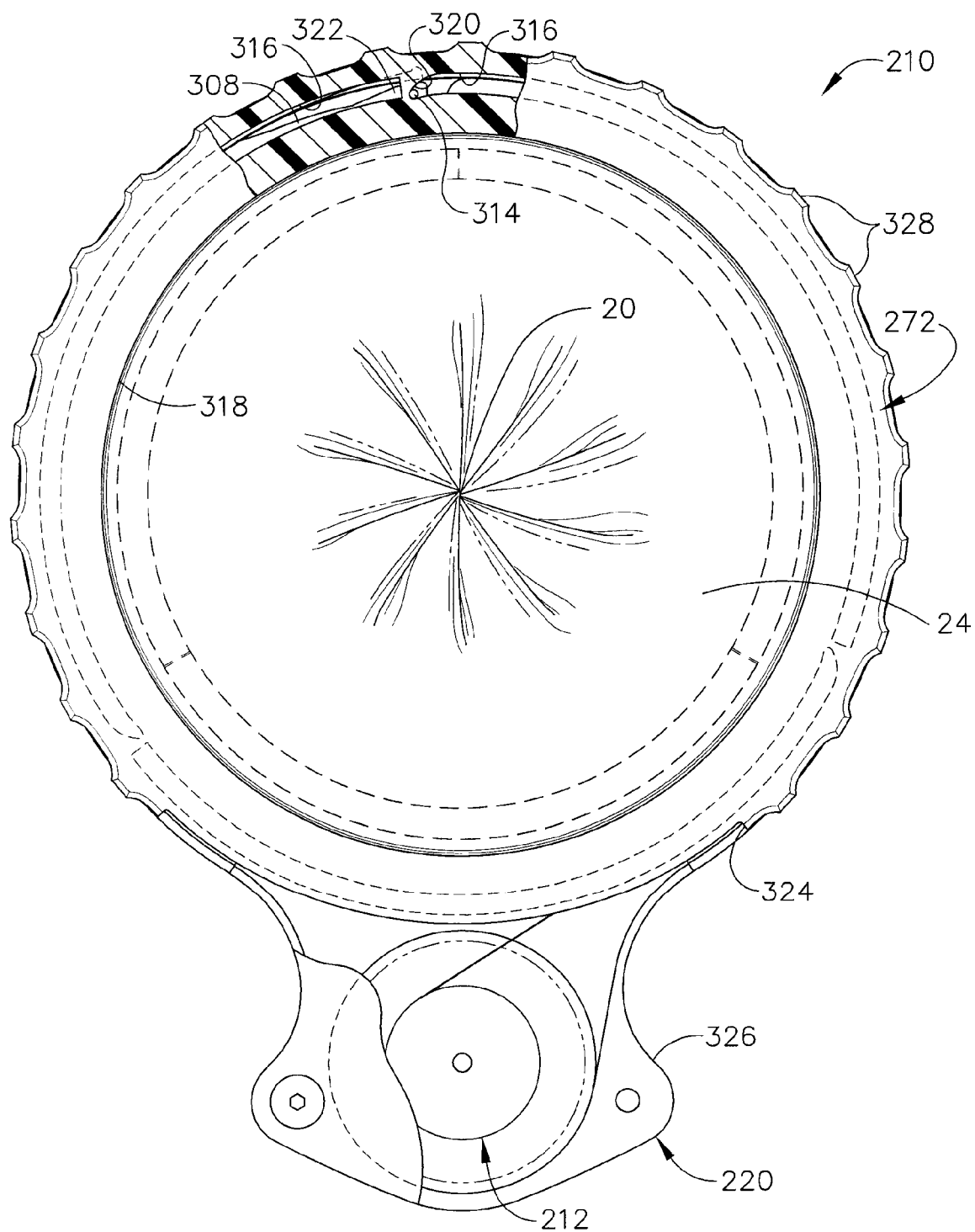
FIG. 35 is a top view of the alternative laparoscopic disk assembly of FIG. 34 partially cut away to expose an upward and small counterclockwise movement of the actuating ring to reposition an upper actuating pin of the opening lock arm to an adjacent arcing groove in the actuating ring to disengage the opening lock arm to release the opening ring for opening back to the state depicted in FIG. 32.

In FIG. 35, with the adjustable access channel 20 closed as previously described, the actuating ring 272 has been lifted while being rotated clockwise so that the upper actuating pin 314 moves from the clockwise termination 322 of one arcing groove 316 to the counterclockwise termination 320 of the adjacent arcing groove 316 that is clockwise thereto. Further clockwise movement of the actuating ring 272 that draws the upper actuating pin 314 radially inward disengages the opening lock arm 308 from the upper ratchet recess 312, allowing the upper motor spring 212 to rotate the opening ring 216 clockwise, untwisting the twist seal 24, until the opening lock arm 308 engages the next upper ratchet recess 312 approximately after one third of a rotation.

It should be appreciated that other unlocking implementations may be incorporated to selectively open and to selectively close the twist seal 24. Further, it should be appreciated that rather than one third of a rotation, other spacing of ratchet recess may be incorporated into applications consistent with aspects of the invention, such as 1 or 2. Furthermore, while the upper motor spring 212 enhances the opening time of the lap disk assembly 210, it should be appreciated that the stored torsional energy in the twist seal 24 may be sufficient to effect opening without the assistance of the motor spring 212 nor of the compression springs.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

While the present invention has been illustrated by description of several embodiments and while the illustrative embodiments have been described in considerable detail, it is not the intention of the applicant to restrict or in any way limit the scope of the appended claims to such detail. Additional advantages and modifications may readily appear to those skilled in the art.

Figure 36:
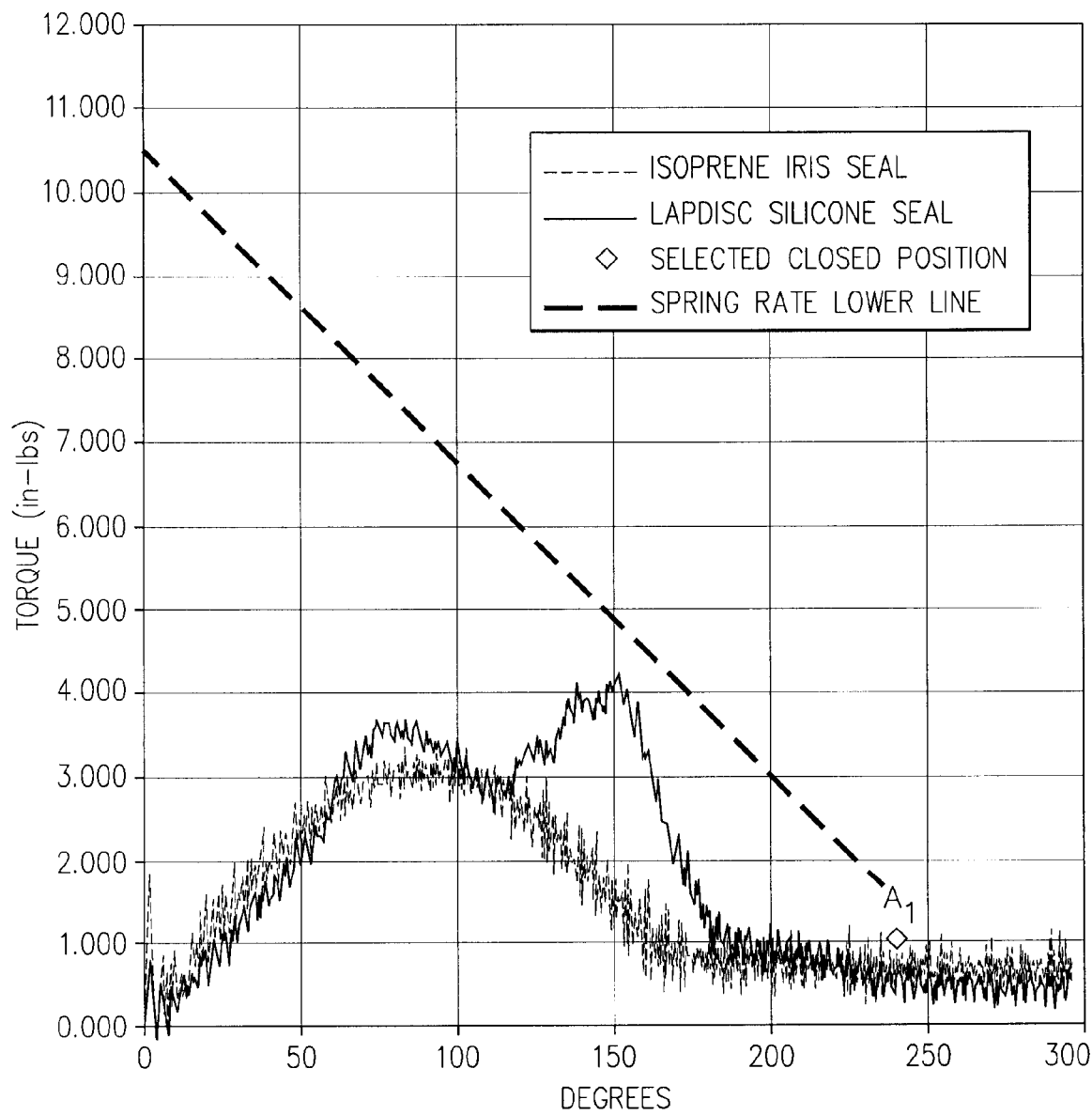
FIG. 36 is a plot diagram of measured reactive torque force of two types of twist seals as a function of a twist angle and a linear approximation of a power source transfer function for overcoming the reactive torque.

For example, while a passive biasing spring (e.g., motor spring) is depicted in the illustrative versions, applications consistent with aspects of the present invention may incorporate a powered source such as constant power source motor, battery, or pneumatics. The selected power source would provide closing power in excess of the reactive torque generated by the twist seal (e.g., isoprene, silicon), such as depicted in FIG. 36.

What is claimed is:

1. A surgical access device, comprising:
   a tubular diaphragm;
   a first annular member circularly coupled to a first end of the tubular diaphragm;
   a second annular member circularly coupled to a second end of the tubular diaphragm, wherein the second annular member is selectively rotatable relative to the first annular member;
   a third annular member configured to selectively engage the second annular member to restrict rotation of the second annular member relative to the first annular member, wherein the third annular member is selectively rotatable relative to the first annular member, wherein the third annular member is further configured to selectively engage the first annular member to restrict rotation of the third annular member relative to the first annular member, wherein the first, second, and third annular members are aligned along a common axis;
   a housing aligning the first and second annular members for relative rotation between an open condition and a closed condition of the tubular diaphragm, wherein the first annular member is fixed relative to the housing; and
   a closing biasing member connected between the housing and the third annular member, wherein the closing biasing member resiliently biases the third annular member to engage the second annular member to impart a closing rotation to the second annular member to effect the closed condition of the tubular diaphragm;
   wherein the second annular member is rotatable relative to the first and third annular members to disengage the third annular member from the first annular member, wherein the third annular member is configured to drive the second annular member to a closed rotational position in response to the resilient bias from the closing biasing member when the third annular member is disengaged from the first annular member by rotation of the second annular member, further comprising an opening biasing member coupled between the first and second annular member operatively configured to store energy to impart an opposite opening relative rotation between the first and second annular member.

2. The surgical access device of claim 1, wherein the tubular diaphragm comprises a resilient material selected to store torsional energy when twisted to the closed condition sufficient to impart an opposite opening relative rotation between the first and second annular members.

3. The surgical access device of claim 1, further comprising an opening biasing member coupled between the housing and the first annular member.

4. The surgical access device of claim 3, wherein the opening biasing member comprises a motor spring.

5. The surgical access device of claim 1, wherein the housing further comprises a retractor skirt attached to the housing and communicating with the tubular diaphragm.

6. The surgical access device of claim 1, wherein the closing biasing member comprises a motor spring.

7. The surgical access device of claim 1, further comprising a ratcheting mechanism positioned to allow a winding rotation of the second annular member opposite to the closing rotation.

8. The surgical access device of claim 7, further comprising a winding tool inserted into the housing to effect the winding rotation of the second annular member.

9. The surgical access device of claim 1, further comprising:
   a ratchet pawl and ratchet recess engageable between a selected two of a group consisting of the first annular member, the second annular member and the housing, and
   an actuator operatively configured to release the pawl from the ratchet recess to enable relative motion between the selected two.

10. A surgical access device, comprising:
    a tubular diaphragm;

an opening ring circularly coupled to a first end of the tubular diaphragm, wherein the opening ring has an exterior;

a stationary ring circularly coupled to a second end of the tubular diaphragm, wherein the stationary ring has an exterior;

a closure ring, wherein the closure ring is positioned about the exterior of the opening ring and about the exterior of the stationary ring;

a housing aligning the opening and stationary rings for relative rotation between an open condition and a closed condition of the tubular diaphragm, wherein the stationary ring is fixed relative to the housing, wherein the opening ring and the closure ring are each rotatable relative to the housing, wherein the opening ring is rotatable concomitantly with the closure ring in a first direction, wherein the opening ring is rotatable independently relative to the closure ring in a second direction;

a closing biasing member connected between the housing and the closure ring to impart a closing rotation to the closure ring to drive the opening ring to effect the closed condition of the tubular diaphragm;

an opening biasing member coupled between the opening and stationary ring to store a restoring force during closing rotation of the closure ring and opening ring;

a resilient member, wherein the resilient member is operatively configured to selectively engage the closure ring to block closing rotation of the closure ring when the resilient member is in a first position, wherein the resilient member is resiliently biased toward the first position, wherein the resilient member is movable to a second position to disengage the closure ring to permit closing rotation of the closure ring; and an actuating member operatively configured to move the resilient member to the second position for allowing the closing biasing member to impart a closing rotation to the closure ring, wherein the actuating member is further operatively configured to release the opening ring from the closure ring after closing to allow the opening biasing member to effect opening of the tubular diaphragm.

11. The surgical access device of claim 10, further comprising a winding actuator operatively coupled to the closure ring to effect a winding rotation opposite to the closing rotation.

12. The surgical access device of claim 10, wherein the opening biasing member comprises a spring having one end confined by the stationary ring and another end confined by the housing.

13. The surgical access device of claim 10, wherein the housing further comprises a retractor skirt attached to the housing and communicating with the tubular diaphragm.

14. The surgical access device of claim 10, wherein the closing biasing member comprises a motor spring.

15. A surgical access device, comprising:

a tubular diaphragm;

a first annular member circularly coupled to a first end of the tubular diaphragm;

a second annular member circularly coupled to a second end of the tubular diaphragm;

a housing aligning the first and second annular members for relative rotation between an open condition and a closed condition of the tubular diaphragm, the first annular member being fixed relative to the housing;

a closing biasing member connected between the housing and the second annular member to impart a closing rotation to the second annular member to effect the closed condition of the tubular diaphragm, wherein the closing biasing member is biased to urge the second annular member to a closed rotational position;

a first locking member restraining the second annular member from rotating in an opening direction relative to the first annular member, wherein the first locking member permits the second annular member to rotate in the closing direction relative to the first annular member, wherein the first locking member comprises a first resilient arm extending outwardly from the second annular member, wherein the first resilient arm is movable inwardly from a blocking position to a non-blocking position, wherein the first resilient arm is resiliently biased toward the blocking position, wherein the first resilient arm restrains the second annular member from rotating in an opening direction when the first resilient arm is in the blocking position, wherein the first resilient arm permits the second annular member to rotate in the opening direction when the first resilient arm is in the non-blocking position;

a second locking member selectively restraining the closing biasing member from driving the second annular member in a closing direction relative to the first annular member, wherein the second locking member comprises a second resilient arm extending outwardly from the first annular member, wherein the second resilient arm is configured to selectively engage or disengage the closing biasing member, wherein the second locking member permits the second annular member to rotate in the opening direction relative to the first annular member; and a control member operable to selectively release the first and second locking members to effect opening and closing.

16. The surgical access device of claim 15, wherein the closing biasing member comprises a motor spring.

17. The surgical access device of claim 15, further comprising an opening biasing member connected between the first annular member and the second annular member to impart an opening rotation to the second annular member to effect the open condition.

18. The surgical access device of claim 17, wherein the opening biasing member comprises a motor spring.

19. The surgical access device of claim 15, wherein the tubular diaphragm comprises a resilient material selected to store torsional energy when twisted to the closed condition sufficient to impart an opposite opening relative rotation between the first and second annular members.

\* \* \* \* \*